US010689457B2

(12) United States Patent
Paton et al.

(10) Patent No.: US 10,689,457 B2
(45) Date of Patent: Jun. 23, 2020

(54) TREATMENT OF METASTATIC BREAST CANCER

(71) Applicant: Genentech, Inc., South San Francisco, CA (US)

(72) Inventors: Virginia Paton, Piedmont, CA (US); Anne Blackwood Chirchir, Emerald Hills, CA (US); Pam Klein, San Mateo, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/293,165

(22) Filed: Oct. 13, 2016

(65) Prior Publication Data

US 2017/0029527 A1 Feb. 2, 2017

Related U.S. Application Data

(63) Continuation of application No. 14/519,675, filed on Oct. 21, 2014, now abandoned, which is a continuation of application No. 13/632,881, filed on Oct. 1, 2012, now abandoned, which is a continuation of application No. 12/484,440, filed on Jun. 15, 2009, now abandoned.

(60) Provisional application No. 61/061,962, filed on Jun. 16, 2008.

(51) Int. Cl.
| | |
|---|---|
| *A61K 39/395* | (2006.01) |
| *C07K 16/28* | (2006.01) |
| *C07K 16/32* | (2006.01) |
| *C07K 16/30* | (2006.01) |
| *A61K 31/337* | (2006.01) |
| *A61K 45/06* | (2006.01) |
| *A61K 39/00* | (2006.01) |

(52) U.S. Cl.
CPC ........ *C07K 16/3015* (2013.01); *A61K 31/337* (2013.01); *A61K 39/3955* (2013.01); *A61K 39/39558* (2013.01); *A61K 45/06* (2013.01); *C07K 16/2863* (2013.01); *C07K 16/32* (2013.01); *A61K 2039/507* (2013.01); *C07K 2317/21* (2013.01); *C07K 2317/24* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,935,341 A | 6/1990 | Bargmann |
| 4,968,603 A | 11/1990 | Slamon |
| 5,183,884 A | 2/1993 | Kraus |
| 5,401,638 A | 3/1995 | Carney |
| 5,480,968 A | 1/1996 | Kraus |
| 5,514,554 A | 5/1996 | Bacus |
| 5,571,894 A | 11/1996 | Wels |
| 5,587,458 A | 12/1996 | King |
| 5,604,107 A | 2/1997 | Carney |
| 5,641,869 A | 6/1997 | Vandlen |
| 5,648,237 A | 7/1997 | Carter |
| 5,677,171 A | 10/1997 | Hudziak |
| 5,705,157 A | 1/1998 | Greene |
| 5,720,937 A | 2/1998 | Hudziak |
| 5,720,954 A | 2/1998 | Hudziak |
| 5,725,856 A | 3/1998 | Hudziak |
| 5,747,261 A | 5/1998 | King |
| 5,770,195 A | 6/1998 | Hudziak |
| 5,772,997 A | 6/1998 | Hudziak |
| 5,783,186 A | 7/1998 | Arakawa |
| 5,783,404 A | 7/1998 | Koski |
| 5,804,396 A | 9/1998 | Plowman |
| 5,821,337 A | 10/1998 | Carter |
| 5,824,311 A | 10/1998 | Greene |
| 5,837,243 A | 11/1998 | Deo |
| 5,846,749 A | 12/1998 | Slamon |
| 5,856,089 A | 1/1999 | Wang |
| 5,877,305 A | 3/1999 | Huston |
| 5,910,486 A | 6/1999 | Curiel |
| 5,922,845 A | 7/1999 | Deo |

(Continued)

FOREIGN PATENT DOCUMENTS

| | | |
|---|---|---|
| EP | 656367 A1 | 6/1995 |
| EP | 412116 B1 | 11/1995 |

(Continued)

OTHER PUBLICATIONS

Harries et al (Endocrine-Related Cancer, 2002, 9:75-85).*

(Continued)

*Primary Examiner* — Laura B Goddard
(74) *Attorney, Agent, or Firm* — Wendy M. Lee

(57) ABSTRACT

The present invention concerns treatment of previously untreated HER2-positive metastatic breast cancer with a combination of a growth inhibitory HER2 antibody, a HER2 dimerization inhibitor antibody and a taxane. In particular, the invention concerns the treatment of HER2-positiv metastatic breast cancer in patients who did not receive prior chemotherapy or biologic therapy with a HER2 antibody binding essentially to epitope 2C4, a HER2 antibody binding essentially to epitope 4D5, and a taxane. The invention further comprises extending survival of such patients by the combination therapy of the present invention. In a preferred embodiment, the treatment involves administration of trastuzumab, pertuzumab and docetaxel.

5 Claims, 8 Drawing Sheets

Specification includes a Sequence Listing.

(56) References Cited

U.S. PATENT DOCUMENTS

| | | |
|---|---|---|
| 5,925,519 A | 7/1999 | Jennsen |
| 5,939,531 A | 8/1999 | Wels |
| 5,977,322 A | 11/1999 | Marks |
| 5,985,553 A | 11/1999 | King |
| 5,994,071 A | 11/1999 | Ross |
| 6,015,567 A | 1/2000 | Hudziak |
| 6,028,059 A | 2/2000 | Curiel |
| 6,054,297 A | 4/2000 | Carter |
| 6,123,939 A | 9/2000 | Shawver |
| 6,127,526 A | 10/2000 | Blank |
| 6,165,464 A | 12/2000 | Hudziak |
| 6,214,388 B1 | 4/2001 | Benz |
| 6,267,958 B1 | 7/2001 | Andya |
| 6,270,765 B1 | 8/2001 | Deo |
| 6,333,169 B1 | 12/2001 | Hudziak |
| 6,333,348 B1 | 12/2001 | Vogel |
| 6,333,398 B1 | 12/2001 | Blank |
| 6,339,142 B1 | 1/2002 | Basey |
| 6,358,682 B1 | 3/2002 | Jaffee |
| 6,387,371 B1 | 5/2002 | Hudziak |
| 6,395,272 B1 | 5/2002 | Deo |
| 6,399,063 B1 | 6/2002 | Hudziak |
| 6,403,630 B1 | 6/2002 | Dannenberg |
| 6,407,213 B1 | 6/2002 | Carter |
| 6,417,335 B1 | 7/2002 | Basey |
| 6,458,356 B1 | 10/2002 | Arakawa |
| 6,489,447 B1 | 12/2002 | Basey |
| 6,512,097 B1 | 1/2003 | Marks |
| 6,573,043 B1 | 6/2003 | Cohen |
| 6,582,919 B2 | 6/2003 | Danenberg |
| 6,602,670 B2 | 8/2003 | Danenberg |
| 6,627,196 B1 | 9/2003 | Baughman |
| 6,632,979 B2 | 10/2003 | Erickson |
| 6,639,055 B1 | 10/2003 | Carter et al. |
| 6,685,940 B2 | 2/2004 | Andya |
| 6,719,971 B1 | 4/2004 | Carter |
| 6,767,541 B2 | 7/2004 | Slamon |
| 6,797,814 B2 | 9/2004 | Blank |
| 6,800,738 B1 | 10/2004 | Carter |
| 6,821,515 B1 | 11/2004 | Cleland |
| 6,905,830 B2 | 6/2005 | Cohen |
| 6,949,245 B1 | 9/2005 | Sliwkowski |
| 6,984,494 B2 | 1/2006 | Ralph |
| 7,018,809 B1 | 3/2006 | Carter |
| 7,041,292 B1 | 5/2006 | Sliwkowski |
| 7,060,268 B2 | 6/2006 | Andya |
| 7,074,404 B2 | 7/2006 | Basey et al. |
| 7,097,840 B2 | 8/2006 | Erickson et al. |
| 7,129,051 B2 | 10/2006 | Cohen et al. |
| 7,279,287 B2 | 9/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 2/2009 | Adams et al. |
| 7,485,704 B2 | 3/2009 | Fahrner et al. |
| 7,498,030 B2 | 3/2009 | Adams et al. |
| 7,501,122 B2 | 3/2009 | Adams et al. |
| 7,531,645 B2 | 5/2009 | Basey et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,674,589 B2 | 3/2010 | Cohen et al. |
| 7,682,609 B2 | 3/2010 | Andya et al. |
| 7,700,299 B2 | 4/2010 | Moecks et al. |
| 7,807,799 B2 | 5/2010 | Fahrner et al. |
| 7,811,773 B2 | 12/2010 | Ralph |
| 7,846,441 B1 | 12/2010 | Hellmann |
| 7,850,966 B2 | 12/2010 | Lowman et al. |
| 7,862,817 B2 | 1/2011 | Adams et al. |
| 7,879,325 B2 | 1/2011 | Kao et al. |
| 7,892,549 B2 * | 2/2011 | Paton ............... A61K 31/7068 424/130.1 |
| 7,919,254 B2 | 5/2011 | Cohen et al. |
| 7,981,418 B2 | 7/2011 | Amler et al. |
| 7,993,834 B2 | 9/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus |
| 8,337,856 B2 | 12/2012 | Blattler et al. |
| 8,404,234 B2 | 3/2013 | Allison et al. |
| 8,597,654 B2 | 3/2013 | Bryant |
| 8,425,908 B2 | 4/2013 | Hellmann |
| 8,440,402 B2 | 5/2013 | Mass |
| 8,529,901 B2 | 9/2013 | Hasmann et al. |
| 8,604,014 B2 | 10/2013 | Belvin et al. |
| 8,591,897 B2 | 11/2013 | Bryant |
| 8,592,152 B2 | 11/2013 | Mass |
| 8,372,396 B2 | 12/2013 | Andya et al. |
| 8,652,474 B2 | 2/2014 | Harris et al. |
| 8,652,479 B2 | 2/2014 | Ebens, Jr. et al. |
| 8,642,036 B2 | 4/2014 | Hellmann |
| 8,663,643 B2 | 4/2014 | Berry et al. |
| 8,710,196 B2 | 4/2014 | Emery et al. |
| 8,758,747 B2 | 6/2014 | Kallmeyer et al. |
| 8,691,232 B2 | 8/2014 | Derynck et al. |
| 8,840,896 B2 | 9/2014 | Lowman et al. |
| 9,181,346 B2 | 10/2015 | Harris et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,896,478 B2 | 2/2018 | Lebreton et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,385,405 B2 | 8/2019 | Lee-Hoeflich et al. |
| 2001/0014326 A1 | 8/2001 | Andya et al. |
| 2002/0001587 A1 | 1/2002 | Erickson et al. |
| 2002/0031515 A1 | 3/2002 | Caligiuri |
| 2002/0035736 A1 | 3/2002 | Erickson et al. |
| 2002/0051785 A1 | 5/2002 | Slamon |
| 2002/0064785 A1 | 5/2002 | Mass |
| 2002/0076408 A1 | 6/2002 | Buchsbaum |
| 2002/0076695 A1 | 6/2002 | Ross |
| 2002/0090662 A1 | 7/2002 | Ralph |
| 2002/0141993 A1 | 10/2002 | Ashkenazi |
| 2002/0142328 A1 | 10/2002 | Danenberg |
| 2002/0155527 A1 | 10/2002 | Stuart |
| 2002/0192211 A1 | 12/2002 | Hudziak |
| 2002/0192652 A1 | 12/2002 | Danenberg |
| 2003/0022918 A1 | 1/2003 | Horak |
| 2003/0059790 A1 | 3/2003 | Jaffee |
| 2003/0068318 A1 | 4/2003 | O'Brien |
| 2003/0078388 A1 | 4/2003 | Basey et al. |
| 2003/0086924 A1 | 5/2003 | Sliwkowski |
| 2003/0103973 A1 | 6/2003 | Rockwell |
| 2003/0108545 A1 | 6/2003 | Rockwell |
| 2003/0134344 A1 | 7/2003 | Mass |
| 2003/0144252 A1 | 7/2003 | Furr |
| 2003/0147884 A1 | 8/2003 | Paton |
| 2003/0152572 A1 | 8/2003 | Homma |
| 2003/0152987 A1 | 8/2003 | Cohen |
| 2003/0157097 A1 | 8/2003 | Noguchi |
| 2003/0162796 A1 | 8/2003 | Hilberg et al. |
| 2003/0165840 A1 | 9/2003 | Danenberg |
| 2003/0170234 A1 | 9/2003 | Hellmann |
| 2003/0170235 A1 | 9/2003 | Cohen |
| 2003/0175845 A1 | 9/2003 | Kalbag |
| 2003/0190689 A1 | 10/2003 | Crosby |
| 2003/0202972 A1 | 10/2003 | Andya et al. |
| 2003/0202973 A1 | 10/2003 | Pieczenik |

(56) References Cited

U.S. PATENT DOCUMENTS

| | | |
|---|---|---|
| 2003/0211530 A1 | 11/2003 | Danenberg |
| 2003/0228663 A1 | 12/2003 | Lowman |
| 2004/0013297 A1 | 1/2004 | Taipei |
| 2004/0013667 A1 | 1/2004 | Kelsey |
| 2004/0024815 A1 | 2/2004 | Kawase |
| 2004/0037823 A9 | 2/2004 | Paton et al. |
| 2004/0082047 A1 | 4/2004 | Emery |
| 2004/0106161 A1 | 6/2004 | Bossenmaier |
| 2004/0138160 A1 | 7/2004 | Naito |
| 2004/0209290 A1 | 10/2004 | Cobleigh |
| 2004/0236078 A1 | 11/2004 | Carter |
| 2004/0258685 A1 | 12/2004 | Brunetta |
| 2005/0002928 A1 | 1/2005 | Hellmann |
| 2005/0038231 A1 | 2/2005 | Fahrner |
| 2005/0025753 A1 | 3/2005 | Han et al. |
| 2005/0063972 A1 | 3/2005 | Basey |
| 2005/0100944 A1 | 5/2005 | Cohen et al. |
| 2005/0208043 A1 | 9/2005 | Adams |
| 2005/0238640 A1 | 10/2005 | Sliwkowski |
| 2005/0244417 A1 | 11/2005 | Ashkenazi |
| 2005/0244929 A1 | 11/2005 | Carter |
| 2005/0276812 A1 | 12/2005 | Ebens et al. |
| 2006/0013819 A1 | 1/2006 | Kelsey |
| 2006/0018899 A1 | 1/2006 | Kao |
| 2006/0034840 A1 | 2/2006 | Agus |
| 2006/0034842 A1* | 2/2006 | Adams ............... A61K 31/282 424/143.1 |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya |
| 2006/0182739 A1 | 4/2006 | Basey et al. |
| 2006/0165702 A1* | 7/2006 | Allison ............... C07K 16/32 424/155.1 |
| 2006/0275306 A1 | 7/2006 | Andya et al. |
| 2006/0121044 A1 | 8/2006 | Amler et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0099201 A1 | 11/2006 | Andya et al. |
| 2006/0228745 A1 | 12/2006 | Mass |
| 2006/0275305 A1 | 12/2006 | Bryant |
| 2007/0020261 A1 | 1/2007 | Slikowski et al. |
| 2007/0026001 A1 | 1/2007 | Ashkenazi et al. |
| 2007/0037228 A1 | 2/2007 | Moecks et al. |
| 2007/0166753 A1 | 7/2007 | Mass |
| 2007/0202516 A1 | 8/2007 | Mass |
| 2007/0184055 A1 | 9/2007 | Sliwkowski |
| 2007/0224203 A1 | 9/2007 | Friess et al. |
| 2007/0009976 A1 | 11/2007 | Lenz et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen et al. |
| 2008/0050385 A1 | 2/2008 | Friess et al. |
| 2008/0050748 A1 | 2/2008 | Cohen et al. |
| 2008/0241146 A1 | 2/2008 | Ashkenazi et al. |
| 2008/0160026 A1 | 3/2008 | Ashkenazi et al. |
| 2008/0102069 A1 | 5/2008 | Freiss et al. |
| 2008/0108096 A1 | 5/2008 | Ralph |
| 2008/0112957 A1 | 5/2008 | Fendly et al. |
| 2008/0112958 A1 | 5/2008 | Mass |
| 2008/0171040 A1 | 7/2008 | Ebens et al. |
| 2008/0187533 A1 | 8/2008 | Hellmann |
| 2008/0226659 A1 | 9/2008 | Erickson et al. |
| 2008/0286280 A1 | 11/2008 | Kallmeyer et al. |
| 2008/0317753 A1 | 12/2008 | Amler et al. |
| 2009/0087432 A1 | 2/2009 | Sliwkowski |
| 2009/0081223 A1 | 3/2009 | Allison et al. |
| 2009/0098135 A1 | 4/2009 | Belvin et al. |
| 2009/0099344 A1 | 4/2009 | Fahrner et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0220492 A1 | 9/2009 | Basey et al. |
| 2009/0226455 A1 | 9/2009 | Filvaroff |
| 2009/0239236 A1 | 9/2009 | Mass |
| 2009/0148402 A1 | 11/2009 | Brunetta et al. |
| 2009/0148435 A1 | 11/2009 | Lebreton et al. |
| 2009/0285837 A1 | 11/2009 | Kao et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0120053 A1 | 5/2010 | Cohen et al. |
| 2010/0196363 A1 | 5/2010 | Vanhauwere et al. |
| 2010/0112603 A1 | 6/2010 | Moecks et al. |
| 2010/0158899 A1 | 6/2010 | Andya et al. |
| 2010/0285010 A1 | 11/2010 | Friess et al. |
| 2010/0298156 A1 | 11/2010 | Lee-Hoeflich et al. |
| 2011/0033460 A1 | 2/2011 | Fendly et al. |
| 2011/0044977 A1 | 2/2011 | Adler et al. |
| 2011/0027190 A1 | 3/2011 | Hasmann et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0151454 A1 | 6/2011 | Lee-Hoeflich et al. |
| 2011/0165157 A1 | 7/2011 | Derynck et al. |
| 2011/0223159 A1 | 9/2011 | Thomas et al. |
| 2011/0223619 A1 | 9/2011 | Belvin et al. |
| 2011/0236383 A1 | 9/2011 | Andya et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |
| 2012/0065381 A1 | 3/2012 | Emery et al. |
| 2012/0093838 A1 | 4/2012 | Mass |
| 2012/0107302 A1 | 5/2012 | Berry et al. |
| 2012/0107391 A1 | 5/2012 | Kelsey |
| 2012/0121586 A1 | 5/2012 | Kiermaier et al. |
| 2012/0251530 A1 | 10/2012 | Sliwkowski et al. |
| 2013/0039909 A1 | 2/2013 | Amler et al. |
| 2013/0071384 A1 | 3/2013 | Andya et al. |
| 2013/0095172 A1 | 4/2013 | Alavattam et al. |
| 2013/0108620 A1 | 5/2013 | Blattler et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0195845 A1 | 8/2013 | Fendly et al. |
| 2013/0195851 A1 | 8/2013 | Alavattam et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0323180 A1 | 12/2013 | Hasmann et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 4/2014 | Dobosz et al. |
| 2014/0128580 A1 | 5/2014 | Ebens, Jr. et al. |
| 2014/0140993 A1 | 5/2014 | Ross et al. |
| 2014/0186343 A1 | 7/2014 | Harris et al. |
| 2014/0186347 A1 | 7/2014 | Derynck et al. |
| 2014/0186867 A1 | 7/2014 | Harris et al. |
| 2014/0212411 A1 | 7/2014 | Blattler et al. |
| 2014/0227255 A1 | 8/2014 | Bauss et al. |
| 2014/0248274 A1 | 9/2014 | Kallmeyer et al. |
| 2014/0248609 A1 | 9/2014 | Mass |
| 2014/0308277 A1 | 10/2014 | Gennaro et al. |
| 2014/0322202 A1 | 10/2014 | Cohen |
| 2014/0341886 A1 | 11/2014 | Hellmann |
| 2016/0175438 A1 | 6/2016 | Alavattam et al. |

(56) References Cited

U.S. PATENT DOCUMENTS

| | | |
|---|---|---|
| 2016/0376377 A1 | 12/2016 | Basey et al. |
| 2017/0029527 A1 | 2/2017 | Paton et al. |
| 2017/0037147 A1 | 2/2017 | Allison et al. |
| 2017/0073777 A1 | 3/2017 | Lee-Hoeflich et al. |
| 2017/0136026 A1 | 5/2017 | Sliwkowski et al. |
| 2017/0166656 A1 | 6/2017 | Lowman et al. |
| 2017/0190786 A1 | 6/2017 | Fendly et al. |
| 2017/0035907 A1 | 9/2017 | Green et al. |
| 2017/0008971 A1 | 12/2017 | Dennis et al. |
| 2018/0282428 A1 | 4/2018 | Fendly et al. |
| 2018/0118781 A1 | 5/2018 | Lebreton et al. |
| 2018/0134803 A1 | 5/2018 | Douthwaite et al. |
| 2018/0162951 A1 | 6/2018 | Cohen |
| 2018/0250397 A1 | 6/2018 | Benyunes et al. |
| 2018/0201692 A1 | 7/2018 | Lowman et al. |
| 2018/0037622 A1 | 8/2018 | Gennaro et al. |
| 2018/0037660 A1 | 8/2018 | Gennaro et al. |
| 2018/0037661 A1 | 8/2018 | Gennaro et al. |
| 2018/0228895 A1 | 8/2018 | Adler et al. |
| 2018/0236072 A1 | 8/2018 | Derynck et al. |
| 2018/0236093 A1 | 8/2018 | Bryant |
| 2018/0244715 A1 | 8/2018 | Emery et al. |
| 2018/0221481 A1 | 9/2018 | Beattie et al. |
| 2018/0221488 A1 | 9/2018 | Andya et al. |
| 2018/0251557 A1 | 9/2018 | Chui et al. |
| 2018/0274038 A1 | 9/2018 | Belousov et al. |
| 2018/0280408 A1 | 10/2018 | Belvin et al. |
| 2018/0296470 A1 | 10/2018 | Eng-Wong et al. |
| 2018/0327510 A1 | 11/2018 | Allison et al. |
| 2019/0055317 A1 | 2/2019 | Baughman et al. |
| 2019/0070291 A1 | 3/2019 | Mass |
| 2019/0117769 A1 | 4/2019 | Benyunes et al. |
| 2019/0240185 A1 | 8/2019 | Desmond-Hellmann et al. |

FOREIGN PATENT DOCUMENTS

| | | | |
|---|---|---|---|
| EP | | 494135 B1 | 4/1996 |
| EP | | 502812 B1 | 8/1996 |
| EP | | 711565 | 8/1998 |
| EP | | 554441 B1 | 1/1999 |
| EP | | 616812 B1 | 11/1999 |
| EP | | 1006194 A2 | 6/2000 |
| EP | | 444181 B1 | 10/2001 |
| EP | | 1357132 | 10/2003 |
| WO | WO 87/07646 | | 12/1987 |
| WO | WO 89/10412 | | 11/1989 |
| WO | WO 91/02062 A2 | | 2/1991 |
| WO | WO 91/05264 | | 4/1991 |
| WO | WO 93/03741 A1 | | 3/1993 |
| WO | WO 93/12220 A1 | | 6/1993 |
| WO | WO 93/16185 A2 | | 8/1993 |
| WO | WO 93/21232 A1 | | 10/1993 |
| WO | WO 93/21319 A1 | | 10/1993 |
| WO | WO 94/00136 A1 | | 1/1994 |
| WO | WO 94/22478 A1 | | 10/1994 |
| WO | WO 96/07321 A1 | | 3/1996 |
| WO | WO 96/16673 A1 | | 6/1996 |
| WO | WO 96/40789 A1 | | 12/1996 |
| WO | WO 97/00271 A1 | | 1/1997 |
| WO | WO 97/20858 A1 | | 6/1997 |
| WO | WO 97/38731 A1 | | 10/1997 |
| WO | WO 98/02463 A1 | | 1/1998 |
| WO | WO 98/17797 A1 | | 4/1998 |
| WO | WO 98/18489 A1 | | 5/1998 |
| WO | WO 98/33914 A1 | | 8/1998 |
| WO | WO 98/45479 A1 | | 10/1998 |
| WO | WO 99/31140 A1 | | 6/1999 |
| WO | WO 99/48527 A1 | | 9/1999 |
| WO | WO 99/55367 A1 | | 11/1999 |
| WO | WO 00/61145 A1 | | 10/2000 |
| WO | WO 00/61185 A1 | | 10/2000 |
| WO | WO 00/69460 A1 | | 11/2000 |
| WO | WO 00/78347 A1 | | 12/2000 |
| WO | WO 01/000238 A1 | | 1/2001 |
| WO | WO 01/000244 A2 | | 1/2001 |
| WO | WO 01/000245 A2 | | 1/2001 |
| WO | WO 01/005425 A2 | | 1/2001 |
| WO | WO 01/009187 A2 | | 2/2001 |
| WO | WO 01/15730 A1 | | 3/2001 |
| WO | WO 01/20033 A1 | | 3/2001 |
| WO | WO 01/21192 A2 | | 3/2001 |
| WO | WO 01/76586 A1 | | 4/2001 |
| WO | WO 01/32155 A2 | | 5/2001 |
| WO | WO 01/53354 A2 | | 7/2001 |
| WO | WO 01/56604 A1 | | 8/2001 |
| WO | WO 01/64246 A2 | | 9/2001 |
| WO | WO 01/76630 A1 | | 10/2001 |
| WO | WO 01/87334 A1 | | 11/2001 |
| WO | WO 01/87336 A1 | | 11/2001 |
| WO | WO 01/89566 A1 | | 11/2001 |
| WO | WO 02/005791 A2 | | 1/2002 |
| WO | WO 02/09754 A1 | | 2/2002 |
| WO | WO 02/11677 A2 | | 2/2002 |
| WO | WO 02/44413 A2 | | 6/2002 |
| WO | WO 02/45653 A2 | | 6/2002 |
| WO | WO 02/055106 A2 | | 7/2002 |
| WO | WO 02/070008 A1 | | 9/2002 |
| WO | WO 02/087619 A1 | | 11/2002 |
| WO | WO 02/089842 A1 | | 11/2002 |
| WO | WO 03/006509 A2 | | 1/2003 |
| WO | WO 03/012072 A2 | | 2/2003 |
| WO | WO 03/028638 A2 | | 4/2003 |
| WO | WO 03/040404 A1 | | 5/2003 |
| WO | WO 03/041736 A2 | | 5/2003 |
| WO | WO 03/078662 A1 | | 9/2003 |
| WO | WO 03/86467 A1 | | 10/2003 |
| WO | WO 03/087131 A2 | | 10/2003 |
| WO | WO 04/008099 A2 | | 1/2004 |
| WO | WO 04/008099 A2 | | 1/2004 |
| WO | WO 04/04866 A2 | | 3/2004 |
| WO | WO 04/048525 A2 | | 6/2004 |
| WO | WO 04/053497 A2 | | 6/2004 |
| WO | WO 04/063709 A2 | | 7/2004 |
| WO | WO 04/065583 A2 | | 8/2004 |
| WO | WO 04/000094 A2 | | 12/2004 |
| WO | WO 05/16968 | | 2/2005 |
| WO | WO 05/099756 | | 10/2005 |
| WO | WO 06/07398 | | 1/2006 |
| WO | WO 06/33700 | | 3/2006 |
| WO | WO 06/091693 A2 | | 8/2006 |
| WO | WO 07/013950 A2 | | 2/2007 |
| WO | WO 08/031531 | | 3/2008 |
| WO | WO 08/109440 | | 9/2008 |
| WO | 2018/085513 A1 | | 5/2018 |
| WO | 2018/125589 A1 | | 7/2018 |
| WO | 2018/160654 | | 9/2018 |

OTHER PUBLICATIONS

De Maio et al (BMC Cancer, 2007, 7:50, internet pp. 1-9).*
Wardley et al (Breast Cancer Research and Treatment, 2006, 100:S101-S102, Abstract #2063).*
Raff et al (Clinical Breast Cancer, 2004, 4:420-427).*
Burris III et al (Seminars in Oncology, 2001, 28:Suppl 3:38-44).*
Walshe et al (Clinical Breast Cancer, 2006, 6:535-539).*
Nahta et al (Cancer Research, 2004, 64:2343-2346).*
Harries and Smith (Endocrine-Related Cancer, 2002, 9:75-85).*
Attard et al (British Jounral of Cancer, 2007, 97:1338-1343).*
Kem et al., *Cancer Res.*, 50:5184 (1990).
Yonemura et al., *Cancer Res.*, 51:1034 (1991).
Aasland et al. *Br. J, Cancer* 57:358-363 (1988).
Agus et al. *Cancer Cell* 2:127-37 (2002).
Agus et al. *Pro Am Soc Clin Oncol* 22:192 (2003).
Allison et al. *Pro Am Soc Clin Oncol* 22:197 (2003).
Arpino, et al., "Complete disappearance of ER+/HER2+ breast cancer xenografts with the combination of gefitinib, trastuzumab, and pertuzumab to block HER2 cross-talk with ER and restore tamoxifen inhibition", Breast Cancer Research and Treatment, vol. 88, Suppl.1, p. S15, (2004) Abstract.
Arpino, et al., "Treatment of human epidermal growth factor receptor 2—Overexpressing breast cancer xenografts with multiagent HER-Targeted therapy", JNCI, vol. 99, Issue 9, pp. 694-705, (2007).

(56) References Cited

OTHER PUBLICATIONS

Arteaga et al. *Cancer Res.* 54:3758-3765 (1994).
Bacus et al. *Cancer Research* 52:2580-2589 (1992).
Bacus et al. *Molecular Carcinogenesis* 3:350-362 (1990).
Baselga et al., *J. Clin. Oncol.* 14:737-744 (1996).
Borst et al, *Gynecol. Oncol.*, 38:364 (1990).
Brand, et al., "Prospect for anti-Her2 receptor therapy in breast cancer", Anticancer Research, 26:715-722, (2006).
Cho et al. *Nature* 421:756-60 (2003).
Cohen et al., *Oncogene*, 4:81-88 (1989).
Cronin et al. *Am. J. Path.* 164(1): 35-42 (2004).
Drebin et al. *Oncogene* 2:273-277 (1988).
Drebin et al., *Cell* 41:695-706 (1985).
Fendly et al. *Cancer Research* 50:1550-1558 (1990).
Friedman, et al., "Synergistic down-regulation of receptor tyrosine kinases by combinations of mAbs: Implications for cancer immunotherapy", PNAS, vol. 102, No. 6, pp. 1915-1920, (2005).
Fukushige et al., *Mol Cell Biol.*, 6:955-958 (1986).
Gu et al. *Cancer Letters.* 99:185-9 (1996).
Guerin et al, *Oncogene Res.*,3:21-31 (1988).
Hancock et al. *Cancer Res.* 51:4575-4580 (1991).
Harari and Yarden *Oncogene* 19:6102-14 (2000).
Harwerth et al. *J. Biol. Chem.* 267:15160-15167 (1992).
Hudziak ei al., *Mol. Cell. Biol.* 9(3):1165-1172 (1989).
Kasprzyk et al. *Cancer Research* 52:2771-2776 (1992).
Kern et al., *Cancer Res.*, 50:5184 (1990).
King et al, *Science*, 229:974 (1985).
Klapper et al. *Oncogene* 14:2099-2109 (1997).
Kotts et al. *In Vitro* 26(3):59A (1990).
Kumar et al. *Mol. Cell. Biol.* 11(2):979-986 (1991).
Lewis et al. *Cancer Research* 56:1457-1465 (1996).
Kumar, et al., "HER2 targeted therapy in breast cancer . . . beyond Herceptin", Rev. Endocr. Metab. Disord., 8:269-277, (2007).
Meden, et al., "Weekly intravenous recombinant humanized Anti-P185$^{HER2}$monoclonal antibody (Herceptin) plus docetaxel in patients with metastatic breast cancer: A pilot study", Anticancer Research, 21:1301-1306, (2001).
Nahta, et al., "The Her-2-targeting antibodies trastuzumab and pertuzumab synergistically inhibit the survival of breast cancer cells", Cancer Research, 64:2343-2346, (2004).
Lewis et al.*Cancer Immunol. Immunoiher.* 37:255-263 (1993).
Ma et al. *Cancer Cell* 5:607-616 (2004).
Maier et al.*Cancer Res.* 51:5361-5369 (1991).
Malik et al. *Pro Am Soc Cancer Res* 44:176-7 (2003).
McCann et al, *Cancer,* 65:88-92 (1990).
McKenzie et al. *Oncogene* 4:543-548 (1989).
Myers et al., *Meth. Enzym.* 198:277-290 (1991).
Park et al., *Cancer Res.*, 49:6605 (1989).
Pietras et al. *Oncogene* 9:1829-1838 (1994).
Ross et al. *Hum. Pathol.* 28:827-33 (1997).
Ross et al. *Cancer* 79:2162-70 (1997).
Sadasivan et al. *J. Urol.* 150:126-31 (1993).
Sarup et al. *Growth Regulation* 1:72-82 (1991).
Schaefer et al. *Oncogene* 15:1385-1394 (1997).
Scott ei al. *J. Biol. Chem.* 266:14300-5 (1991).
Shawver et al. *Cancer Res.* 54:1367-1373 (1994).
Shepard et al. *J Clin. Immunol.* 11(3):117-127 (1991).
Slamon et al. *Science,* 235:177-182 (1987).
Slamon et al., *Science*,244:707-712 (1989).
Sliwkowski et al. *J. Biol. Chem.* 269(20):1466114665 (1994).
Sliwkowski *Nat Struct Biol* 10:158-9 (2003).

Stancovski et al.*JWAS (USA)* 88:8691-8695 (1991).
Tagliabue et al. *Int. Cancer* 47:933-937 (1991).
Vitetta et al. *Cancer Research* 54:5301-5309 (1994).
Weiner et al, *Cancer Res.*, 50:421-425 (1990).
Williams et al. *Pathobiology* 59:46-52 (1991).
Xu et al. *Int. J. Cancer* 53:401-408 (1993).
Yarden and Sliwkowski. *Nat Rev Mol Cell Biol* 2:127-37 (2001).
Yokota et at, *Lancet:* 1:765-767 (1986).
Yonemura et a/., *Cancer Res.*, 51:1034 (1991).
Zhau et al., *Mol. Carcinog.*, 3:254-257 (1990).
"A study to evaluate Pertuzumab + Trastuzumab + Docetaxel vs. Placebo + Transtuzumab + Docetaxel in previous untreated Her2-positive metastatic breast cancer (CLEOPATRA).", Clinical Trials. gov, Publication Date Dec. 3, 2007.
Baselga et al., "Pertuzumab plus Trastuzumab plus Docetaxel for Metastatic Breast Cancer" New England Journal of Medicine, (10.1056/NEJMoa1113216) Dec. 7, 2011, 11 pgs.
Bullock et al., "Clinical efficacy of taxane-trastuzumab combination regimens for HER-2-positive metastatic breast cancer" ONCOLOGIST 13:515-525 ( 2008).
Genentech, Inc., CLEOPATRA Protocol: A Study to Evaluate Pertuzumab + Trastuzumab + Docetaxel vs. Placebo + Trastuzumab + Docetaxel in Previously Untreated Her2-Postitive Metastatic Breast Cancer (CLEOPATRA), pp. 1-11, http://clinicaltrials.gov/ct2/show/NCT00567190, pp. 1-11 (first posted Dec. 4, 2007, downloaded Jul. 23, 2019).
ClinicalTrials.gov, "A Study to Evaluate Pertuzumab + Trastuzumab + Docetaxel vs. Placebo + Trastuzumab + Docetaxel in Previously Untreated HER2-Positive Metastatic Breast Cancer (CLEOPATRA)" (Pertuzumab + Trastuzumab + Docetaxel vs. Placebo + Trastuzumab + Docetaxel; NCT00567190; First Posted: Dec. 4, 2007; Last Update Posted: Dec. 13, 2019; Printed: Jan 21, 2020),:1-20 https://clinicaltrials.gov/ct2/show/NCT00567190.
Fabi et al., "First-line therapy in HER2 positive metastatic breast cancer: is the mosaic fully completed or are we missing additional pieces?" Journal of Experimental & Clinical Cancer Research 35(104) (2016).
Genentech Inc., "Pertuzumab combined with Herceptin and chemotherapy significantly extended the time people with HER2-positive metastatic breast cancer lived without their disease getting worse" (press release retrieved from the Internet Jan. 17, 2013),:1-4 (Jul. 14, 2011) http://www.gene.com/media/press-releases/13547/2011-07-14/pertuzumab-combined-with-herceptin-and-c/.
Lenihan et al., "Pooled analysis of cardiac safety in patients with cancer treated with pertuzumab" Annals of Oncology 23(3):791-800 (Mar. 2012).
"Pertuzumab (PERJETA) United States Prescribing Information (USPI)":1-14 (Jun. 2012) https://www.accessdata.fda.gov/drugsatfda_docs/label/2012/125409Ibl.pdf.
"Pertuzumab (PERJETA) United States Prescribing Information (USPI),":1-36 (Jan. 2020)—Pertuzumab (PERJETA) United States Prescribing Information (USPI).
Portera et al., "Cardiac toxicity and efficacy of trastuzumab combined with pertuzumab in patients with Trastuzumab-insensitive human epidermal growth factor receptor 2-positive metastatic breast cancer" Clinical Cancer Research 14(9):2710-2716 (May 1, 2008).
Swain et al., "Pertuzumab, Trastuzumab, and Docetaxel in HER2-Positive Metastatic Breast Cancer" N Engl J Med 372:724-34 ( 2015).
"Trastuzumab (HERCEPTIN) United States Prescribing Information (USPI)":1-11 (Jan. 2008) https://www.accessdata.fda.gov/drugsatfda_docs/label/2008/103792s5175Ibl.pdf.

* cited by examiner

Variable Light

```
              10          20             30              40
2C4    DTVMTQSHKIMSTSVGDRVSITC  [KASQDVSIGVA]  WYQQRP
         **  **** *          *                         *
574    DIQMTQSPSSLSASVGDRVTITC  [KASQDVSIGVA]  WYQQKP
                                  *   * hum κI DIQMTQSPSSLSASVGDRVTITC  [RASQSISNYLA]  WYQQKP 50              60            70           80
2C4    GQSPKLLIY  [SASYRYT]  GVPDRFTGSGSGTDFTFTISSVQA
         **                      *  *          *    * *
574    GKAPKLLIY  [SASYRYT]  GVPSRFSGSGSGTDFTLTISSLQP
                   * ***** hum κI GKAPKLLIY  [AASSLES]  GVPSRFSGSGSGTDFTLTISSLQP 90            100
2C4    EDLAVYYC  [QQYYIYPYT]  FGGGTKLEIK  (SEQ ID NO:1)
         * *                     *  *
574    EDFATYYC  [QQYYIYPYT]  FGQGTKVEIK  (SEQ ID NO:3)
                   *** * hum κI EDFATYYC  [QQYNSLPWT]  FGQGTKVEIK  (SEQ ID NO:5)
```

FIG. 2A

Variable Heavy

```
              10          20              30            40
2C4    EVQLQQSGPELVKPGTSVKISCKAS  [GFTFTDYTMD]  WVKQS
          **  **  *  * ***    *                       * *
574    EVQLVESGGGLVQPGGSLRLSCAAS  [GFTFTDYTMD]  WVRQA
                                     ** * * hum III EVQLVESGGGLVQPGGSLRLSCAAS [GFTFSSYAMS]  WVRQA 50       a      60              70           80
2C4    HGKSLEWIG  [DVNPNSGGSIYNQRFKG]  KASLTVDRSSRIVYM
        *  *   **                       *** *     **** *
574    PGKGLEWVA  [DVNPNSGGSIYNQRFKG]  RFTLSVDRSKNTLYL
                   **** * ****      *  * hum III PGKGLEWVA [VISGDGGSTYYADSVKG]  RFTISRDNSKNTLYL abc        90          100ab         110
2C4    ELRSLTFEDTAVYYCAR  [NLGPSFYFDY]  WGQGTTLTVSS  (SEQ ID NO:2)
        ***  **                                **
574    QMNSLRAEDTAVYYCAR  [NLGPSFYFDY]  WGQGTLVTVSS  (SEQ ID NO:4)
                           ******** hum III QMNSLRAEDTAVYYCAR [GRVGYSLYDY]  WGQGTLVTVSS  (SEQ ID NO:6)
```

FIG. 2B

Amino Acid Sequence for Pertuzumab Light Chain

```
          10        20        30        40        50        60
DIQMTQSPSSLSASVGDRVTITCKASQDVSIGVAWYQQKPGKAPKLLIYSASYRYTGVPS
          70        80        90       100       110       120
RFSGSGSGTDFTLTISSLQPEDFATYYCQQYYIYPYTFGQGTKVEIKRTVAAPSVFIFPP
         130       140       150       160       170       180
SDEQLKSGTASVVCLLNNFYPREAKVQWKVDNALQSGNSQESVTEQDSKDSTYSLSSTLT
         190       200       210
LSKADYEKHKVYACEVTHQGLSSPVTKSFNRGEC
```

*FIG. 3A*

Amino Acid Sequence for Pertuzumab Heavy Chain

```
          10        20        30        40        50        60
EVQLVESGGGLVQPGGSLRLSCAASGFTFTDYTMDWVRQAPGKGLEWVADVNPNSGGSIY
          70        80        90       100       110       120
NQRFKGRFTLSVDRSKNTLYLQMNSLRAEDTAVYYCARNLGPSFYFDYWGQGTLVTVSSA
         130       140       150       160       170       180
STKGPSVFPLAPSSKSTSGGTAALGCLVKDYFPEPVTVSWNSGALTSGVHTFPAVLQSSG
         190       200       210       220       230       240
LYSLSSVVTVPSSSLGTQTYICNVNHKPSNTKVDKKVEPKSCDKTHTCPPCPAPELLGGP
         250       260       270       280       290       300
                                                            *
SVFLFPPKPKDTLMISRTPEVTCVVVDVSHEDPEVKFNWYVDGVEVHNAKTKPREEQYNS
         310       320       330       340       350       360
TYRVVSVLTVLHQDWLNGKEYKCKVSNKALPAPIEKTISKAKGQPREPQVYTLPPSREEM
         370       380       390       400       410       420
TKNQVSLTCLVKGFYPSDIAVEWESNGQPENNYKTTPPVLDSDGSFFLYSKLTVDKSRWQ
         430       440      448
QGNVFSCSVMHEALHNHYTQKSLSLSPG
```

*FIG. 3B*

Light Chain

```
1                          15                          30                          45
DIQMTQSPSSLSASVGDRVTITCRASQDVNTAVAWYQQKPGKAPK 46                         60                          75                          90
LLIYSASFLYSGVPSRFSGSRSGTDFTLTISSLQPEDFATYYCQQ 91                         105                         120                         135
HYTTPPTFGQGTKVEIKRTVAAPSVFIFPPSDEQLKSGTASVVCL 136                        150                         165                         180
LNNFYPREAKVQWKVDNALQSGNSQESVTEQDSKDSTYSLSSTLT 181                        195                         210    214
LSKADYEKHKVYACEVTHQGLSSPVTKSFNRGEC
```

FIG. 4A

Heavy Chain

```
  1 EVQLVESGGGLVQPGGSLRLSCAASGFNIKDTYIHWVRQAPGKGL
 46 EWVARIYPTNGYTRYADSVKGRFTISADTSKNTAYLQMNSLRAED
 91 TAVYYCSRWGGDGFYAMDYWGQGTLVTVSSASTKGPSVFPLAPSS
136 KSTSGGTAALGCLVKDYFPEPVTVSWNSGALTSGVHTFPAVLQSS
181 GLYSLSSVVTVPSSSLGTQTYICNVNHKPSNTKVDKKVEPKSCDK
226 THTCPPCPAPELLGGPSVFLFPPKPKDTLMISRTPEVTCVVVDVS
271 HEDPEVKFNWYVDGVEVHNAKTKPREEQYNSTYRVVSVLTVLHQD
316 WLNGKEYKCKVSNKALPAPIEKTISKAKGQPREPQVYTLPPSREE
361 MTKNQVSLTCLVKGFYPSDIAVEWESNGQPENNYKTTPPVLDSDG
406 SFFLYSKLTVDKSRWQQGNVFSCSVMHEALHNHYTQKSLSLSPG
```

FIG. 4B

```
1   VHSDIQMTQSPSSLSASVGDRVTITCKASQDVSIGVAWYQQKPGK
                 15                30              45
46  APKLLIYSASYRYTGVPSRFSGSGSGTDFTLTISSLQPEDFATYY
              60              75              90
91  CQQYYIYPYTFGQGTKVEIKRTVAAPSVFIFPPSDEQLKSGTASV
              105             120             135
136 VCLLNNFYPREAKVQWKVDNALQSGNSQESVTEQDSKDSTYSLSS
              150             165             180
181 TLTLSKADYEKHKVYACEVTHQGLSSPVTKSFNRGEC
              195             210    217
```

Serum Pertuzumab Concentrations (μg/mL) for the First 84 Days (through Study Day 85) for Studies TOC2689g and BO16934

SEQUENCE LISTING

<160> NUMBER OF SEQ ID NOS: 23

<210> SEQ ID NO 1
<211> LENGTH: 107
<212> TYPE: PRT
<213> ORGANISM: Mus sp.

<400> SEQUENCE: 1

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 2
<211> LENGTH: 119
<212> TYPE: PRT
<213> ORGANISM: Mus sp.

<400> SEQUENCE: 2

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
        50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105

<210> SEQ ID NO 6
<211> LENGTH: 119
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

-continued

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 8
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Any amino acid

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Xaa Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 9
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 11
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 12
<211> LENGTH: 449
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13

<400> SEQUENCE: 13

000

<210> SEQ ID NO 14
<211> LENGTH: 195
<212> TYPE: PRT
<213> ORGANISM: Homo sapiens

<400> SEQUENCE: 14

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg
        195

<210> SEQ ID NO 15
<211> LENGTH: 124
<212> TYPE: PRT
<213> ORGANISM: Homo sapiens

<400> SEQUENCE: 15

Thr Val Cys Ala Gly Gly Cys Ala Arg Cys Lys Gly Pro Leu Pro Thr
1               5                   10                  15

Asp Cys Cys His Glu Gln Cys Ala Ala Gly Cys Thr Gly Pro Lys His
            20                  25                  30
```

Ser Asp Cys Leu Ala Cys Leu His Phe Asn His Ser Gly Ile Cys Glu
            35                  40                  45

Leu His Cys Pro Ala Leu Val Thr Tyr Asn Thr Asp Thr Phe Glu Ser
 50                  55                  60

Met Pro Asn Pro Glu Gly Arg Tyr Thr Phe Gly Ala Ser Cys Val Thr
 65                  70                  75                  80

Ala Cys Pro Tyr Asn Tyr Leu Ser Thr Asp Val Gly Ser Cys Thr Leu
                 85                  90                  95

Val Cys Pro Leu His Asn Gln Glu Val Thr Ala Glu Asp Gly Thr Gln
                100                 105                 110

Arg Cys Glu Lys Cys Ser Lys Pro Cys Ala Arg Val
                115                 120

<210> SEQ ID NO 16
<211> LENGTH: 169
<212> TYPE: PRT
<213> ORGANISM: Homo sapiens

<400> SEQUENCE: 16

Cys Tyr Gly Leu Gly Met Glu His Leu Arg Glu Val Arg Ala Val Thr
 1               5                  10                  15

Ser Ala Asn Ile Gln Glu Phe Ala Gly Cys Lys Lys Ile Phe Gly Ser
                 20                  25                  30

Leu Ala Phe Leu Pro Glu Ser Phe Asp Gly Asp Pro Ala Ser Asn Thr
            35                  40                  45

Ala Pro Leu Gln Pro Glu Gln Leu Gln Val Phe Glu Thr Leu Glu Glu
 50                  55                  60

Ile Thr Gly Tyr Leu Tyr Ile Ser Ala Trp Pro Asp Ser Leu Pro Asp
 65                  70                  75                  80

Leu Ser Val Phe Gln Asn Leu Gln Val Ile Arg Gly Arg Ile Leu His
                 85                  90                  95

Asn Gly Ala Tyr Ser Leu Thr Leu Gln Gly Leu Gly Ile Ser Trp Leu
                100                 105                 110

Gly Leu Arg Ser Leu Arg Glu Leu Gly Ser Gly Leu Ala Leu Ile His
            115                 120                 125

His Asn Thr His Leu Cys Phe Val His Thr Val Pro Trp Asp Gln Leu
130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165

<210> SEQ ID NO 17
<211> LENGTH: 142
<212> TYPE: PRT
<213> ORGANISM: Homo sapiens

<400> SEQUENCE: 17

Cys His Gln Leu Cys Ala Arg Gly His Cys Trp Gly Pro Gly Pro Thr
 1               5                  10                  15

Gln Cys Val Asn Cys Ser Gln Phe Leu Arg Gly Gln Glu Cys Val Glu
                 20                  25                  30

Glu Cys Arg Val Leu Gln Gly Leu Pro Arg Glu Tyr Val Asn Ala Arg
            35                  40                  45

His Cys Leu Pro Cys His Pro Glu Cys Gln Pro Gln Asn Gly Ser Val
 50                  55                  60

```
Thr Cys Phe Gly Pro Glu Ala Asp Gln Cys Val Ala Cys Ala His Tyr
 65                  70                  75                  80

Lys Asp Pro Pro Phe Cys Val Ala Arg Cys Pro Ser Gly Val Lys Pro
                 85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
        130                 135                 140

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ser or Asp

<400> SEQUENCE: 18

Gly Phe Thr Phe Thr Asp Tyr Thr Met Xaa
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Val Asn Pro Asn Ser Gly Gly Ser Ile Tyr Asn Gln Arg Phe Lys
1               5                   10                  15

Gly

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Leu Gly Pro Ser Phe Tyr Phe Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Ser Gln Asp Val Ser Ile Gly Val Ala
1               5                   10

<210> SEQ ID NO 22
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Tyr or Glu
<220> FEATURE:
<221> NAME/KEY: MOD_RES
<222> LOCATION: (7)..(7)
<223> OTHER INFORMATION: Thr or Ser

<400> SEQUENCE: 22

Ser Ala Ser Tyr Xaa Xaa Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Tyr Tyr Ile Tyr Pro Tyr Thr
1               5
```

TREATMENT OF METASTATIC BREAST CANCER

CROSS-REFERENCE TO RELATED APPLICATIONS

This application is a continuation of U.S. application Ser. No. 14/519,675, filed Oct. 21, 2014, which is a continuation of U.S. application Ser. No. 13/632,881, filed Oct. 1, 2012 (now abandoned), which is a continuation of U.S. application Ser. No. 12/484,440, filed Jun. 15, 2009 (now abandoned), which claims priority under 35 U.S.C. Section 119(e) and the benefit of U.S. Provisional Application No. 61/061,962, filed Jun. 16, 2008, the entire disclosures of which are incorporated herein by reference.

INCORPORATION OF SEQUENCE LISTING

This application includes a Sequence Listing submitted via EFS-Web on Aug. 25, 2009, as a computer-readable form file entitled "SequenceListing.txt" (32 KB) dated Aug. 12, 2009. Which is hereby incorporated herein by reference it its entirety.

FIELD OF THE INVENTION

The present invention concerns treatment of previously untreated HER2-positive metastatic breast cancer with a combination of a growth inhibitory HER2 antibody, a HER2 dimerization inhibitor antibody and a taxane. In particular, the invention concerns the treatment of HER2-positiv metastatic breast cancer in patients who did not receive prior chemotherapy or biologic therapy with a HER2 antibody binding essentially to epitope 2C4, a HER2 antibody binding essentially to epitope 4D5, and a taxane. The invention further comprises extending survival of such patients by the combination therapy of the present invention. In a preferred embodiment, the treatment involves administration of trastuzumab, pertuzumab and docetaxel.

BACKGROUND OF THE INVENTION

HER Receptors and Antibodies Thereagainst

Members of the HER family of receptor tyrosine kinases are important mediators of cell growth, differentiation and survival. The receptor family includes four distinct members including epidermal growth factor receptor (EGFR, ErbB1, or HER1), HER2 (ErbB2 or $p185^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn, supra; Masui et al. *Cancer Research* 44:1002-1007 (1984); and Wu et al. *J. Clin. Invest.* 95:1897-1905 (1995).

The second member of the HER family, $p185^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet:* 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat $p185^{neu}$ and human HER2 protein products have been described.

Drebin and colleagues have raised antibodies against the rat neu gene product, p185neu See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of $p185^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2): 979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors over-express the HER2 protein. While the administration of trastuzumab has led to excellent results in the treatment of breast cancer, recent data from a clinical trial of lapirinib appear to suggest that even with administration of of trastuzumab, HER2 plays an active role in tumor biology (Geyer et al., *N Engl J Med* 2006; 355:2733-2743).

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS (USA)* 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

Patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat. Nos. 5,648,237, 6,267,958, 6,685,940, 6,821,515, WO98/17797, U.S. Pat. Nos. 6,127,526, 6,333,398, 6,797,814, 6,339,142, 6,417,335, 6,489,447, WO99/31140, US2003/0147884A1, US2003/0170234A1, US2004/0037823A1, US2005/0002928A1, U.S. Pat. Nos. 6,573,043, 6,905,830, US2003/0152987A1, WO99/48527, US2002/0141993A1, US2005/0244417A1, U.S. Pat. No. 6,949,245, US2003/0086924, US2004/0013667A1, WO00/69460, US2003/0170235A1, U.S. Pat. No. 7,041,292, WO01/00238, US2006/0083739, WO01/15730, U.S. Pat. No. 6,627,196B1, U.S. Pat. No. 6,632,979B1, WO01/00244, US2002/0001587A1, US2002/0090662A1, U.S. Pat. No. 6,984,494B2, WO01/89566, US2002/0064785, US2003/0134344, WO 2005/099756, US2006/0013819, WO2006/07398A1, US2006/0018899, WO 2006/33700, US2006/0088523, US 2006/0034840, WO 04/24866, US2004/0082047, US2003/0175845A1, WO03/087131, US2003/0228663, WO2004/008099A2, US2004/0106161, WO2004/048525, US2004/0258685A1, WO 2005/16968, US2005/0038231A1 U.S. Pat. Nos. 5,985,553, 5,747,261, 4,935,341, 5,401,638, 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. Nos. 5,571,894, 5,939,531, EP 502,812 B1, WO 93/03741, EP 554,441 B1, EP 656,367 A1, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028,059, WO 96/07321, U.S. Pat. Nos. 5,804,396, 5,846,749, EP 711,565, WO 96/16673, U.S. Pat. Nos. 5,783,404, 5,977,322, 6,512,097, WO 97/00271, U.S. Pat. Nos. 6,270,765, 6,395,272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/

0138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842, and WO 03/86467.

Patients treated with the HER2 antibody trastuzumab are selected for therapy based on HER2 overexpression/amplification. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, U.S. Pat. Nos. 6,573,043, 6,905,830, and US2003/0152987, Cohen et al., concerning immunohistochemistry (IHC) and fluorescence in situ hybridization (FISH) for detecting HER2 overexpression and amplification.

WO2004/053497 and US2004/024815A1 (Bacus et al.), as well as US 2003/0190689 (Crosby and Smith), refer to determining or predicting response to trastuzumab therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290 and WO04/065583, Cobleigh et al., concern gene expression markers for breast cancer prognosis. See, also, WO03/078662 (Baker et al.), and WO03/040404 (Bevilacqua et al.). WO02/44413 (Danenberg, K.) refers to determining EGFR and HER2 gene expression for determining a chemotherapeutic regimen.

Patients treated with pertuzumab can be selected for therapy based on HER activation or dimerization. Patent publications concerning pertuzumab and selection of patients for therapy therewith include: U.S. Pat. No. 6,949,245, WO01/00245, US2005/0208043, US2005/0238640, US2006/0034842, and US2006/0073143 (Adams et al.); US2003/0086924 (Sliwkowski, M.); US2004/0013667A1 (Sliwkowski, M.); as well as WO2004/008099A2, and US2004/0106161 (Bossenmaier et al.).

Cronin et al. *Am. J. Path.* 164(1): 35-42 (2004) describes measurement of gene expression in archival paraffin-embedded tissues. Ma et al. *Cancer Cell* 5:607-616 (2004) describes gene profiling by gene oliogonucleotide microarray using isolated RNA from tumor-tissue sections taken from archived primary biopsies.

Pertuzumab (also known as recombinant human monoclonal antibody 2C4; OMNITARG™, Genentech, Inc, South San Francisco) represents the first in a new class of agents known as HER dimerization inhibitors (HDI) and functions to inhibit the ability of HER2 to form active heterodimers with other HER receptors (such as EGFR/HER1, HER3 and HER4) and is active irrespective of HER2 expression levels. See, for example, Harari and Yarden *Oncogene* 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003).

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

US 2006/0034842 describes methods for treating ErbB-expressing cancer with anti-ErbB2 antibody combinations. WO 08/031531 describes the use of trastuzumab and pertuzumab in the treatment of HER2-positive metastatic cancer, such as breast cancer. Baselga et al., *J Clin Oncol*, 2007 ASCO Annual Meeting Proccedings Part I, Col. 25, No. 18S (June 20 Supplement), 2007:1004 report the treatment of patients with pre-treated HER2 positive breast cancer, which has progressed during treatment with trastuzumab, with a combination of trastuzumab and pertuzumab. Portera et al., *J Clin Oncol*, 2007 ASCO Annual Meeting Proceedings Part I. Vol. 25, No. 18S (June 20 Supplement), 2007:1028 evaluated the efficacy and safety of trastuzumab+pertuzumab combination therapy in HER2-positive breast cancer patients, who had progressive disease on trastuzumab-based therapy. The authors concluded that further evaluation of the efficacy of combination treatment was required to define the oveall risk and benefit of this treatment regimen.

Pertuzumab has been evaluated in Phase II studies in combination with trastuzumab in patients with HER2-positive metastatic breast cancer who have previously received trastuzumab for metastatic disease. One study, conducted by the National cancer Institute (NCI), enrolled 11 patients with previously treated HER2-positive metastatic breast cancer. Two out of the 11 patients exhibited a partial response (PR) (Baselga et al., *J Clin Oncol* 2007 ASCO Annual Meeting Proceedings; 25:18S (June 20 Supplement): 1004.

Breast cancer is the most common cancer in women, with a global prevalence of more than 1 million patients and a mortality rate of approximately 400,000 deaths per year (International Agency for Research on Cancer; http://www-dep.iarc.fr; Globocan 2002). While improved early detection and advances in systemic therapy for early stage disease have resulted in a decline in breast cancer mortality since 1989, metastatic breast cancer (MBC) remains largely incurable with a median survival of approximately 24 months. Factors associated with poor survival include age ≥50 years, visceral disease, shorter disease-free interval (DFI), aneuploid tumors, tumors with a high S-phase fraction, p53 accumulation, low bcl-2 expression, negative hormone receptor status, and positive human epidermal growth factor receptor 2 (HER2) status (Chang J, et al., *Cancer* 2003; 97:545-53).

Although chemotherapy agents, such as anthracyclines, taxanes, alkylating agents, and/or vinca alkaloids, used as single agents, have produced important results in extending the survival of patients with metastatic breast cancer, the rare complete responses are short-lived, and usually the disease continues to progress. (Chung C, Carlson R. *The Oncologist* 2003; 8:514-20; Bernard-Marty C, et al., *The Oncologist* 2003; 9:617-32).

The HER2-antibody trastuzumab is approved for use as monotherapy or in combination with chemotherapy in the metastatic setting, and in combination with chemotherapy as adjuvant treatment for HER2-positive breast cancer. The optimal management of metastatic breast cancer now takes into account not only a patient's general condition, medical history, tumor burden, and receptor status, but also the HER2 status.

A randomized Phase II study evaluated trastuzumab and docetaxel vs. docetaxel alone as a first-line treatment for HER2-positive metastatic breast cancer (Marty et al., *J Clin Oncol* 2005; 23:4265-4274).

Improvement in survival is an important goal in the treatment of patients diagnosed with HER2-positive metastatic breast cancer. Despite advances in cancer therapy, there is significant medical need for new treatment regimens in order to achieve this goal.

SUMMARY OF THE INVENTION

The present invention provides clinical data from human breast cancer patients treated with a a combination of trastuzumab, pertuzumab and docetaxel.

In one aspect, the invention concerns a method for the treatment of breast cancer, comprising administering to a HER2 positive metastatic breast cancer patient an effective amount of a growth inhibitory HER2 antibody, a HER2 dimerization inhibitor antibody, and a taxane, wherein the patient did not receive prior chemotherapy or biologic therapy.

In one embodiment, the growth inhibitory HER2 antibody binds to an epitope within Domain IV (SEQ ID NO: 17) of the HER2 amino acid sequence.

In another embodiment, the growth inhibitory HER2 antibody binds essentially to epitope 4D5 of HER2.

In yet another embodiment, the HER2 dimerization inhibitor antibody binds HER2 at the junction of domains I, II and III (SEQ ID NOs: 14, 15, and 16).

In a further embodiment, the HER2 dimerization inhibitor antibody binds essentially to epitope 2C4.

In a still further embodiment, the growth inhibitory and/or the HER2 dimerization inhibitor antibody is an antibody fragment.

In an additional embodiment, the growth inhibitory and/or the HER2 dimerization inhibitor antibody is chimeric, humanized, or human.

In a particular embodiment, the growth inhibitory antibody is trastuzumab, or a fragrement thereof, the HER2 dimerization antibody is pertuzumab, or a fragment thereof, and the taxane is docetaxel.

In another aspect, the invention concerns a method for the treatment of breast cancer, comprising administering to a HER2 positive metastatic breast cancer patient an effective amount of a first HER2 antibody binding essentially to epitope 2C4, a second HER2 antibody binding essentially to epitope 4D5, and a taxane, wherein the patient did not receive prior chemotherapy or biologic therapy.

In one embodiment, the patient is a human patient.

In another embodiment, the first and second antibodies are monoclonal antibodies.

In yet another embodiment, at least one of the first and the second antibodies is an antibody fragment.

In a different embodiment, at least one of the first and the second antibodies is chimeric humanized, or human.

In a particular embodiment, the first antibody is pertuzumab.

In another particular embodiment, the second antibody is trastuzumab.

In yet another particular embodiment, the taxane is docetaxel.

In a further embodiment, the first and second antibodies and said taxane are administered concurrently.

In a still further embodiment, the first and second antibodies and the taxane are administered consecutively, in any order.

In another embodiment, administration of the first antibody precedes administration of the second antibody and the taxane.

In yet another embodiment, at least one of the pertuzumab and the transtuzumab is a naked antibody.

In a different embodiment, at least one of the pertuzumab and the transtuzumab is an intact antibody.

In a further embodiment, administration of the pertuzumab, trastuzumab and docetaxel results in a synergistic effect.

In a still further embodiment, administration of the pertuzumab, trastuzumab and docetaxel extends survival of the human patient relative to treatment in the absence of at least one of pertuzumab, trastuzumab and docetaxel. In a particular embodiment, progression free survival (PFS) or overall survival (OS) is extended.

Although the methods of the present invention may be performed in the absence of any other means of cancer therapy, e.g. in the absence of a further therapeutic agent, including chemotherapeutic agents and biologics, the methods may optionally comprise the administration of a further therapeutic agent selected from the group consisting of chemotherapeutic agent, a different HER antibody, antibody directed against a tumor associated antigen, anti-hormonal compound, cardioprotectant, cytokine, EGFR-targeted drug, anti-angiogenic agent, tyrosine kinase inhibitor, COX inhibitor, non-steroidal anti-inflammatory drug, farnesyl transferase inhibitor, antibody that binds oncofetal protein CA 125, HER2 vaccine, HER targeting therapy, Raf or ras inhibitor, liposomal doxorubicin, topotecan, taxane, dual tyrosine kinase inhibitor, TLK286, EMD-7200, a medicament that treats nausea, a medicament that prevents or treats skin rash or standard acne therapy, a medicament that treats or prevents diarrhea, a body temperature-reducing medicament, and a hematopoietic growth factor.

In another aspect, the invention concerns a kit comprising a first HER2 antibody binding essentially to epitope 2C4, a second HER2 antibody binding essentially to epitope 4D5, and a taxane, and a package insert or label with directions to treat a HER2 positive metastatic breast cancer patient, who did not receive prior chemotherapy or biologic therap.

In yet another aspect, the invention concers a method of promoting pertuzumab for the treatment of a HER2 positive metastatic breast cancer patient who did not receive prior chemotherapy or biologic therapy, in combination with trastuzumab and a taxane. Just as before the taxane may, for example, be docetaxel.

In a further aspect, the invention concerns a method of promoting trastuzumab for the treatment of a HER2 positive metastatic breast cancer patient who did not receive prior chemotherapy or biologic therapy, in combination with pertuzumab and a taxane, such as docetaxel.

In a still further aspect, the invention concerns a method for promoting a taxane for the treatment of a HER2 positive metastatic breast cancer patient who did not receive prior chemotherapy or biologic therapy, in combination pertuzumab and trastuzumab, wherein the taxane may, for example, be docetaxel. Without limitation, the promotion may be in the form of a written material, or a package insert.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 1 and 2, respectively); $V_L$ and $V_H$ domains of variant 574/pertuzumab (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between variable domains of pertuzumab and murine monoclonal antibody 2C4 or between variable domains of pertuzumab and the human framework. Complementarity Determining Regions (CDRs) are in brackets.

FIGS. 3A and 3B show the amino acid sequences of pertuzumab light chain (FIG. 3A; SEQ ID NO. 7) and heavy chain (FIG. 3B; SEQ ID No. 8). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of trastuzumab light chain (FIG. 4A; SEQ ID NO. 9) and heavy chain (FIG. 4B; SEQ ID NO. 10), respectively.

FIGS. 5A and 5B depict a variant pertuzumab light chain sequence (FIG. 5A; SEQ ID NO. 11) and a variant pertuzumab heavy chain sequence (FIG. 5B; SEQ ID NO. 12), respectively.

DETAILED DESCRIPTION OF THE PREFERRED EMBODIMENTS

I. Definitions

Figure 1:
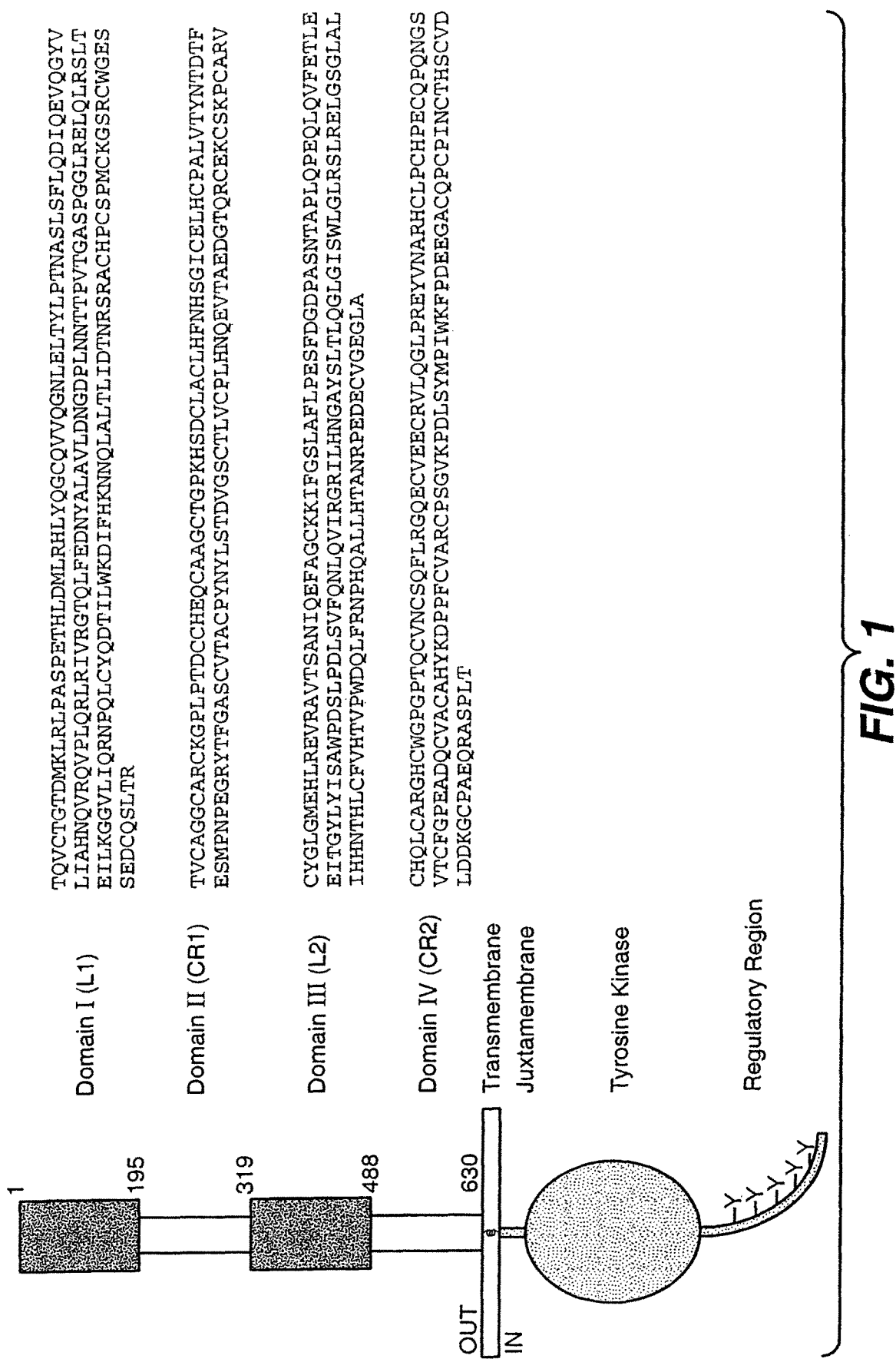
FIG. 1 provides a schematic of the HER2 protein structure, and amino acid sequences for Domains I-IV (SEQ ID Nos.14-17, respectively) of the extracellular domain thereof.

The terms "biologic therapy" "immunotherapy" are used herein interchangeably, and refer to cancer treatments utilizing the body's immune system to fight cancer, regardless of their mechanism of action. Biologic therapy specifically includes antibody treatment.

Ther term "chemotherapy" as used herein refers to treatment comprising the administration of a chemotherapeutic agent, as defined hereinbelow.

"Survival" refers to the patient remaining alive, and includes overall survival as well as progression free survival.

"Overall survival" or "OS" refers to the patient remaining alive for a defined period of time, such as 1 year, 5 years, etc from the time of diagnosis or treatment. For the purposes of the clinical trial described in the examples, overall survival (OS) is defined as the time from the date of randomization of patient population to the date of death from any cause.

"Progression-free survival" or "PFS" refers to the patient remaining alive, without the cancer progressing or getting worse. For the purpose of the clinical trial described in the examples, progression-free survival (PFS) is defined as the time from randomization of study population to the first documented progressive disease, or death from any cause, whichever occurs first. Disease progression can be documented by any clinically accepted methods, such as, for example, radiographical progressive disease, as determined by Response Evaluation Criteria in Solid Tumors (RECIST) (Therasse et al., *J Natl Ca Inst* 2000; 92(3):205-216), carcinomatous meningitis diagnosed by cytologic evaluation of cerebral spinal fluid, and/or medical photography to monitor chest wall recurrences of subcutaneous lesions.

By "extending survival" is meant increasing overall or progression free survival in a patient treated in accordance with the present invention relative to an untreated patient and/or relative to a patient treated with one or more approved anti-tumor agents, but not receiving treatment in accordance with the present invention. In a particular example, "extending survival" means extending progression-free survival (PFS) and/or overall survival (OS) of breast cancer patients receiving the combination therapy of the present invention (e.g. treatment with a combination of a HER2 antibody binding essentially to epitope 2C4, a HER2 antibody binding essentially to epitope 4D5, and a taxane, e.g. pertuzumab+trastuzumab+docetaxel) relative to patients treated with a HER2 antibody binding essentially to epitope 4D5, and a taxane, e.g. trastuzumab+docetaxel, in the absence of a HER2 antibody binding essentially to epitope 2C4, i.e. pertuzumab.

Herein "time to disease progression" or "TTP" refer to the time, generally measured in weeks or months, from the time of initial treatment until the cancer progresses or worsens. Such progression can be evaluated by the skilled clinician. Disease progression can be evaluated and documented by any clinically accepted methods, such as, for example, radiographical progressive disease, as determined by Response Evaluation Criteria in Solid Tumors (RECIST) (Therasse et al., *J Natl Ca Inst* 2000; 92(3):205-216), carcinomatous meningitis diagnosed by cytologic evaluation of cerebral spinal fluid, and/or medical photography to monitor chest wall recurrences of subcutaneous lesions.

By "extending TTP" is meant increasing the time to disease progression in a patient treated in accordance with the present invention relative to an untreated patient and/or relative to a patient treated with one or more approved anti-tumor agents, but not receiving treatment in accordance with the present invention. In a particular example, "extending TTP" means extending time to disease progression (TTP) of breast cancer patients receiving the combination therapy of the present invention (treatment with a combination of a HER2 antibody binding essentially to epitope 2C4, a HER2 antibody binding essentially to epitope 4D5, and a taxane, e.g. pertuzumab+trastuzumab+docetaxel) relative to patients treated with a HER2 antibody binding essentially to epitope 4D5, and a taxane, e.g. trastuzumab+docetaxel, in the absence of a HER2 antibody binding essentially to epitope 2C4, i.e. pertuzumab.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The terms "ErbB1," "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu@ refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1. In one embodiment, the extracellular domain of HER2 may comprise four domains: "Domain I" (amino acid residues from about 1-195; SEQ ID NO:14), "Domain II" (amino acid residues from about 196-319; SEQ ID NO:15), "Domain III" (amino acid residues from about 320-488: SEQ ID NO:16), and "Domain IV" (amino acid residues from about 489-630; SEQ ID NO:17) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 6 herein.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appln No 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)); and cripto (CR-1) (Kaman et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362:312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., J. Biol. Chem., 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER antibody" is an antibody that binds to a HER receptor. Optionally, the HER antibody further interferes with HER activation or function. Preferably, the HER antibody binds to the HER2 receptor. HER2 antibodies of interest herein are pertuzumab and trastuzumab.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384

(2004)); antibodies which bind to HER3 and inhibit dimerization thereof with one or more other HER receptors; and antibodies which bind to HER4 and inhibit dimerization thereof with one or more other HER receptors.

A "HER2 dimerization inhibitor" is an agent that inhibits formation of a dimer or heterodimer comprising HER2.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2 (SEQ ID NO: 15). Franklin et al. *Cancer Cell* 5:317-328 (2004).

A HER2 antibody that "binds to a heterodimeric binding site" of HER2, binds to residues in Domain II (SEQ ID NO: 15) and optionally also binds to residues in other of the domains of the HER2 extracellular domain, such as domains I and III, SEQ ID NOs: 14 and 16), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II (SEQ ID NO: 15) and optionally residues in other domain(s) of HER2, such as domains I and III (SEQ ID NOs: 14 and 16, respectively). Preferably the antibody that binds to domain II binds to the junction between domains I, II and III of HER2.

Protein "expression" refers to conversion of the information encoded in a gene into messenger RNA (mRNA) and then to the protein.

Herein, a sample or cell that "expresses" a protein of interest (such as a HER receptor or HER ligand) is one in which mRNA encoding the protein, or the protein, including fragments thereof, is determined to be present in the sample or cell.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., PCR Technology, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real time polymerase chain reaction" or "qRT-PCR" refers to a form of PCR wherein the amount of PCR product is measured at each step in a PCR reaction. This technique has been described in various publications including Cronin et al., *Am. J. Pathol.* 164(1):35-42 (2004); and Ma et al., *Cancer Cell* 5:607-616 (2004).

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA: DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced also increases in the proportion of the number of copies made of the particular gene expressed.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 &gr;g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "native sequence" polypeptide is one which has the same amino acid sequence as a polypeptide (e.g., HER receptor or HER ligand) derived from nature, including naturally occurring or allelic variants. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers monoclonal antibodies, polyclonal antibodies, multispecific antibodies (e.g. bispecific antibodies), and antibody fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., *Nature*, 352:624-628 (1991); Marks et al., *J. Mol. Biol.*, 222:581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA*, 90:2551(1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include Aprimatized@ antibodies comprising variable domain antigen-binding sequences derived from a non-human primate (e.g. Old World Monkey, Ape etc) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab (HERCEPTIN®) as described in Table 3 of U.S. Pat. No. 5,821,337 expressly incorporated herein by reference; humanized 520C9 (WO93/21319); and humanized 2C4 antibodies such as pertuzumab as described herein.

For the purposes herein, "trastuzumab," "HERCEPTIN®," and "huMAb4D5-8" refer to an antibody comprising the light and heavy chain amino acid sequences in SEQ ID NOs. 9 and 10, respectively.

Herein, "pertuzumab" and "OMNITARG™" refer to an antibody comprising the light and heavy chain amino acid sequences in SEQ ID NOs. 7 and 8, respectively.

An "intact antibody" herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab=fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into Asubclasses@ (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "naked antibody" is an antibody that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than trastuzumab, and/or an antibody which binds to a heterodimeric binding site of HER2. The preferred embodiment herein of the main species antibody is one comprising the variable light and variable heavy amino acid sequences of SEQ ID Nos. 3 and 4, and most preferably comprising the light chain and heavy chain amino acid sequences in SEQ ID Nos. 7 and 8 (pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. deamidated antibody variant), a basic variant, an antibody with an amino-terminal leader extension (e.g. VHS-) on one or two light chains thereof, an antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moeities attached thereto which differ from one or more carbohydate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Where the antibody has an Fc region, an oligosaccharide structure may be attached to one or two heavy chains of the antibody, e.g. at residue 299 (298, Eu numbering of residues). For pertuzumab, G0 was the predominant oligosaccharide structure, with other oligosaccharide structures such as G0-F, G-1, Man5, Man6, G1-1, G1(1-6), G1(1-3) and G2 being found in lesser amounts in the pertuzumab composition.

Unless indicated otherwise, a AG1 oligosaccharide structure@ herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivitized, e.g. to an aspartic acid, a succinimide, or an iso-aspartic acid.

The terms "cancer" and "cancerous" refer to or describe the physiological condition in mammals that is typically characterized by unregulated cell growth. The cancer treated in accordance with the present invention is any type of metastatic HER2 positive breast cancer, including, without limitation, any histologically or cytologically confirmed adenocaracinoma of the breast with locally recurrent or metastatic disease (where the locally recurrent disease is not amenable to resection with curative intent), HER2-positive metastatic ductal carcinoma, HER2-positive metastatic lobular carcinoma, specifically including both ER-positive and ER-negative breast cancers, and may, but are not required to, express other HER receptors, such as EGFR and/or HER3 and/or HER4 and/or one or more HER ligands.

An "advanced" cancer is one which has spread outside the site or organ of origin, either by local invasion or metastasis.

A "refractory" cancer is one which progresses even though an anti-tumor agent, such as a chemotherapeutic agent, is being administered to the cancer patient. An example of a refractory cancer is one which is platinum refractory.

A "recurrent" cancer is one which has regrown, either at the initial site or at a distant site, after a response to initial therapy.

Herein, a "patient" is a human patient. The patient may be a "cancer patient," i.e. one who is suffering or at risk for suffering from one or more symptoms of cancer.

A "tumor sample" herein is a sample derived from, or comprising tumor cells from, a patients tumor, including cancer, as hereinabove defined. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described herein).

Herein, "gene expression profiling" refers to an evaluation of expression of one or more genes as a surrogate for determining HER phosphorylation directly.

A "phospho-ELISA assay" herein is an assay in which phosphorylation of one or more HER receptors, especially HER2, is evaluated in an enzyme-linked immunosorbent assay (ELISA) using a reagent, usually an antibody, to detect phosphorylated HER receptor, substrate, or downstream signaling molecule. Preferably, an antibody which detects phosphorylated HER2 is used. The assay may be performed on cell lysates, preferably from fresh or frozen biological samples.

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; MC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress or amplify HER receptor" is one which does not have higher than normal levels of HER receptor protein or gene compared to a noncancerous cell of the same tissue type. Antibodies that inhibit HER dimerization, such as pertuzumab, may be used to treat cancer which does not overexpress or amplify HER2 receptor.

Herein, an "anti-tumor agent" refers to a drug used to treat cancer. Non-limiting examples of anti-tumor agents herein include chemotherapeutic agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

An "approved anti-tumor agent" is a drug used to treat cancer which has been accorded marketing approval by a regulatory authority such as the Food and Drug Administration (FDA) or foreign equivalent thereof.

Where a HER dimerization inhibitor is administered as a "single anti-tumor agent" it is the only anti-tumor agent administered to treat the cancer, i.e. it is not administered in combination with another anti-tumor agent, such as chemotherapy.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind essentially to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Domain II (SEQ ID NO: 15) in the extracellular domain of HER2. 2C4 and pertuzumab binds to the extracellular domain of HER2 at the junction of domains I, II and III (SEQ ID NOs: 14, 15, and 16, respectively). Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2 (SEQ ID NO: 17). To screen for antibodies which bind essentially to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds essentially to the 4D5 epitope of HER2 (e.g. any one or more residues in the region from about residue 529 to about residue 625, inclusive of the HER2 ECD, residue numbering including signal peptide).

The "epitope 7C2/7F3" is the region at the N terminus, within Domain I (SEQ ID NO: 14), of the extracellular domain of HER2 to which the 7C2 and/or 7F3 antibodies (each deposited with the ATCC, see below) bind. To screen for antibodies which bind essentially to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds essentially to the 7C2/7F3 epitope on HER2 (e.g. any one or more of residues in the region from about residue 22 to about residue 53 of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete respose, CR), increase overall survival time, and/or improve one or more symptoms of cancer (e.g. as assessed by FOSI).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSARC®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e. g., calicheamicin, especially calicheamicin gammaII and calicheamicin omegaII (see, e.g., Agnew, *Chem Intl. Ed. Engl.*, 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX™, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK7 polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

An "antimetabolite chemotherapeutic agent" is an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZARC®), 5-fluorouracil (5-FU), capecitabine (XELODA®), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARAC®), cladrabine, 2-deoxy-D-glucose etc. The preferred antimetabolite chemotherapeutic agent is gemcitabine.

"Gemcitabine" or A"2'-deoxy-2',2'-difluorocytidine monohydrochloride (b-isomer)" is a nucleoside analogue that exhibits antitumor activity. The empirical formula for gemcitabine HCl is C9H11F2N3O4 A HCl. Gemcitabine HCl is sold by Eli Lilly under the trademark GEMZAR®.

A "platinum-based chemotherapeutic agent" comprises an organic compound which contains platinum as an integral part of the molecule. Examples of platinum-based chemotherapeutic agents include carboplatin, cisplatin, and oxaliplatinum.

By "platinum-based chemotherapy" is intended therapy with one or more platinum-based chemotherapeutic agents, optionally in combination with one or more other chemotherapeutic agents.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

By "platinum-resistant" cancer is meant that the cancer patient has progressed while receiving platinum-based chemotherapy (i.e. the patient is "platinum refractory"), or the patient has progressed within 12 months (for instance, within 6 months) after completing a platinum-based chemotherapy regimen.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., *J. Biol. Chem.* 279 (29):30375-30384 (2004)). The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA; Astra Zeneca); CP-358774 or Erlotinib (TARCEVA™; Genentech/OSI); and AG1478, AG1571 (SU 5271; Sugen); EMD-7200.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevac™) available from Glaxo; MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

II. Production of Antibodies

The HER antigen to be used for production of antibodies may be, e.g., a soluble form of the extracellular domain of a HER receptor or a portion thereof, containing the desired epitope. Alternatively, cells expressing HER at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER receptor useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N═C═NR, where R and R$^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Various methods for making monoclonal antibodies herein are available in the art. For example, the monoclonal antibodies may be made using the hybridoma method first described by Kohler et al., *Nature,* 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001(1984); and Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.,* 130:151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222: 581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901(1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

U.S. Pat. No. 6,949,245 describes production of exemplary humanized HER2 antibodies which bind HER2 and block ligand activation of a HER receptor. A humanized antibody used in the methods of the present invention is rhuMAb 2C4 (pertuzumab), or an antibody that binds essentially to the same epitope within the HER2 extracellular domain as pertuzumab. In other embodiments, one of the antibodies used in the methods of the present invention blocks EGF, TGF-α and/or HRG mediated activation of MAPK essentially as effectively as murine monoclonal antibody 2C4 (or a Fab fragment thereof) and/or binds HER2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX (SEQ ID NO: 18), where X is preferably D or S; DVNPNSGGSIYNQRFKG (SEQ ID NO:19); and/or NLGPSFYFDY (SEQ ID NO:20), optionally comprising amino acid modifications of those CDR residues, e.g. where the modifications essentially maintain or improve affinity of the antibody. For example, an antibody variant for use in the methods of the present invention may have from about one to about seven or about five amino acid substitutions in the above variable heavy CDR sequences. Such antibody variants may be prepared by affinity maturation, e.g., as described below.

The humanized antibody may comprise variable light domain complementarity determining residues KASQD-VSIGVA (SEQ ID NO:21); SASYX$^1$X$^2$X$^3$, where X$^1$ is preferably R or L, X$^2$ is preferably Y or E, and X$^3$ is preferably T or S (SEQ ID NO:22); and/or QQYYIYPYT (SEQ ID NO:23), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below.

The present application also contemplates affinity matured antibodies which bind HER2. The parent antibody may be a human antibody or a humanized antibody, e.g., one comprising the variable light and/or variable heavy sequences of SEQ ID Nos. 7 and 8, respectively (i.e. comprising the VL and/or VH of pertuzumab). An affinity matured variant of pertuzumab preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Humanization of murine 4D5 antibody to generate humanized variants thereof, including trastuzumab, is described in U.S. Pat. Nos. 5,821,337, 6,054,297, 6,407,213, 6,639,055, 6,719,971, and 6,800,738, as well as Carter et al. PNAS (USA), 89:4285-4289 (1992). HuMAb4D5-8 (trastuzumab) bound HER2 antigen 3-fold more tightly than the mouse 4D5 antibody, and had secondary immune function (ADCC) which allowed for directed cytotoxic activity of the humanized antibody in the presence of human effector cells. HuMAb4D5-8 comprised variable light (V$_L$) CDR residues incorporated in a V$_L$ κ subgroup I consensuse framework, and variable heavy (V$_H$) CDR residues incorporated into a V$_H$ subgroup III consensus framework. The antibody further comprised framework region (FR) substitutions as positions: 71, 73, 78, and 93 of the V$_H$ (Kabat numbering of FR residues; and a FR substitution at position 66 of the V$_L$ (Kabat numbering of FR residues). Trastuzumab comprises non-A allotype human γ 1 Fc region.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807. Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain FAT fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81(1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in U.S. Pat. No. 6,949,245. HER2 monoclonal antibodies may be added to each well and incubated for 30 minutes. 125I-labeled rHRGβ1177-224 (25 pm) may then be added, and the incubation may be continued for 4 to 16 hours. Dose response curves may be prepared and an IC50 value may be calculated for the antibody of interest. In one embodiment, the antibody which blocks ligand activation of a HER receptor will have an IC50 for inhibiting HRG binding to MCF7 cells in this assay of about 50 nM or less, more preferably 10 nM or less. Where the antibody is an antibody fragment such as a Fab fragment, the IC50 for inhibiting HRG binding to MCF7 cells in this assay may, for example, be about 100 nM or less, more preferably 50 nM or less.

Alternatively, or additionally, the ability of an antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in U.S. Pat. No. 6,949,245. For example, the MCF7 cells may be plated in 24-well plates and monoclonal antibodies to HER2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at $M_r$–180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of a HER receptor will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385-1394 (1997). According to this assay, MDA-MB-175 cells may be treated with a HER2 monoclonal antibody (10 m/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the HER2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(ix) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 3 and 4, and most preferably comprising a light chain amino acid sequence of SEQ ID No. 7, and a heavy chain amino acid sequence of SEQ ID No. 8 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab=)2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

(x) Trastuzumab Compositions

The trastuzumab composition generally comprises a mixture of a main species antibody (comprising light and heavy chain sequences of SEQ ID NOS: 9 and 10, respectively), and variant forms thereof, in particular acidic variants (including deamidated variants). Preferably, the amount of such acidic variants in the composition is less than about 25%. See, U.S. Pat. No. 6,339,142. See, also, Harris et al., J. Chromatography, B 752:233-245 (2001) concerning forms of trastuzumab resolvable by cation-exchange chromatography, including Peak A (Asn30 deamidated to Asp in both light chains); Peak B (Asn55 deamidated to isoAsp in one heavy chain); Peak 1 (Asn30 deamidated to Asp in one light chain); Peak 2 (Asn30 deamidated to Asp in one light chain, and Asp102 isomerized to isoAsp in one heavy chain); Peak 3 (main peak form, or main species antibody); Peak 4 (Asp102 isomerized to isoAsp in one heavy chain); and Peak C (Asp102 succinimide (Asu) in one heavy chain). Such variant forms and compositions are included in the invention herein.

(xi) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-5H3 and reacted with modified antibody (Chari et al. Cancer Research 52: 127-131(1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^T$, $\alpha 2^T$, $\alpha_3^T$, N-acetyl-$\gamma_T^1$, PSAG and $\theta^T_1$ (Hinman et al. Cancer Research 53: 3336-3342 (1993) and Lode et al. Cancer Research 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a Acleavable linker@facilitating release of the cytotoxic drug in the cell. For example, an acid-labile linker, peptidase-sensitive linker, dimethyl linker or disulfide-containing linker (Chari et al. Cancer Research 52: 127-131(1992)) may be used.

Alternatively, a fusion protein comprising the antibody and cytotoxic agent may be made, e.g. by recombinant techniques or peptide synthesis.

Other immunoconjugates are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in *Remington's Pharmaceutical Sciences,* 16th edition, Oslo, A., Ed., (1980).

The antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.*81(19) 1484 (1989).

(xii) Docetaxel

Docetaxel is an anti-neoplastic agent that binds to free tubulin and promotes the assembly of tubulin into stable microtubules while simultaneously inhibiting their assembly. This leads to the production of microtubule bundles without normal function and to the stabilization of microtubules, blocking cells in the M-phase of the cell cycle and leading to cell death.

III. Selecting Patients for Therapy

The present invention concerns the treatment of patients who have HER2-positive metastatic breast cancer and have not received prior chemotherapy or biologic therapy (including approved or investigational tyrosine kinase/HER inhibitors or vaccines) for their metastatic disease. Patient could have received one prior hormonal treatment for metastatic breast cancer. Patients may have received systemic breast cancer treatment in the neo-adjuvant or adjuvant setting, provided that the patient has experienced a disease-free interval (DFI) of ≥12 months from completion of adjuvant systemic treatment (excluding hormonal therapy) to metastatic diagnosis. Patients may have received trastuzumab and/or a taxane during the neo-adjuvant or adjuvant treatment.

Detection of HER2 protein overexpression is important for selection of patients for treatment in accordance with the present invention. Several FDA-approved commercial assays are available to identify breast cancer patients whose cancer overexpresses HER2. These methods include HERCEPTEST™ (Dako) and PATHWAY® HER-2/neu (immunohistochemistry (IHC) assays) and PathVysion® and HER2 FISH pharmDx™ (FISH assays). Users should refer to the package inserts of specific assay kits for information on the validation and performance of each assay.

For example, HER2 overexpression may be analyzed byIHC, e.g. using the HERCEPTEST® (Dako). Paraffin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)).

The presence of HER2 protein overexpression and gene amplification are highly correlated, therefore, alternatively, or additionally, the use of FISH assays to detect gene amplification may also be employed for selection of patients appropriate for treatment in accordance with the present invention. FISH assays such as the INFORM™ (sold by Ventana, Ariz.) or PathVysion® (Vysis, Ill.) may be carried out on formalin-fixed, paraffin-embedded tumor tissue to determine the extent (if any) of HER2 amplification in the tumor.

Most commonly, HER2-positive status is confirmed using archival paraffin-embedded tumor tissue, using any of the foregoing methods.

Preferably, HER2-positive patients having a 3+IHC score or a ≥2.0 FISH amplification ratio are selected for treatment in accordance with the present invention.

IV. Pharmaceutical Formulations

Therapeutic formulations of the HER2 antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride;

phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801, expressly incorporated herein by reference.

Lyophilized antibody formulations are described in U.S. Pat. Nos. 6,267,958, 6,685,940 and 6,821,515, expressly incorporated herein by reference. The preferred HERCEPTN® (trastuzumab) formulation is a sterile, white to pale yellow preservative-free lyophilized powder for intravenous (IV) administration, comprising 440 mg trastuzumab, 400 mg .alpha$\alpha,\alpha$-trehalose dihyrate, 9.9 mg L-histidine-HCl, 6.4 mg L-histidine, and 1.8 mg polysorbate 20, USP. Reconstitution of 20 mL of bacteriostatic water for injection (BWFI), containing 1.1% benzyl alcohol as a preservative, yields a multi-dose solution containing 21 mg/mL trastuzumab, at pH of approximately 6.0. For further details, see the trastuzumab prescribing information.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

The formulation of the placebo used in the clinical trials described in the Examples is equivalent to pertuzumab, without the active agent.

The formulation herein may also contain more than one active compound as necessary for the particular indication being treated, preferably those with complementary activities that do not adversely affect each other. Various drugs which can be combined with the HER dimerization inhibitor are described in the Method Section below. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment Methods

The treatment methods of the present invention comprise, consist essentially of, or consist of the administration of a growth inhibitory HER2 antibody, a HER2 dimerization inhibitor antibody and a taxane. In a particular embodiment, the treatment methods of the present invention comprise, consist essentially of, or consist of the administration of an antibody binding essentially to epitope 2C4, a HER2 antibody binding essentially to epitope 4D5, and a taxane to HER2 positive metastatic breast cancer patients as hereinabove defined, who did not receive prior chemotherapy or biologic therapy for their metastatic disease. In a preferred embodiment, the treatment comprises, consists essentially of or consists of treatment with pertuzumab+trastuzumab+docetaxel. The treatment methods herein may result in a synergistic, or greater than additive, therapeutic benefit to the patient.

Therapy in accordance with the present invention extends progression-free survival (PFS) and/ot overall survival (OS) of the patient treatment. In one embodiment, the treatment extends PFS or OS at least about 5%, or at least about 10%, or at least about 15% or at least about 20%, or at least about 25% more than PFS or OS achieved by administering trastuzumab+docetaxel to the metastatic breast cancer patient to be treated.

Antibodies binding essentially to epitope 2C4 specifically include, without limitation, rhuMAb 2C4 (pertuzumab). Antibodies binding essentially to epitope 4D5 specifically include, without limitation, huMAb4D5-1, huMAb4D5-2, huMAb4D5-3, huMAb4D5-4, huMAb4D5-5, huMAb4D5-6, huMAb4D5-7 and huMAb4D5-8 (trastuzumab).

The antibodies and taxane, such as pertuzumab, trastuzumab, and docetaxel are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. For antibodies, Intravenous administration is preferred.

According to one preferred embodiment of the invention, a fixed dose of HER dimerization inhibitor (e.g. pertuzumab) of approximately 840 mg (loading dose) is administered, followed by one or more doses of approximately 420 mg (maintenance dose(s)) of the antibody. The maintenance doses are preferably administered about every 3 weeks, for a total of at least two doses, until radiographic or clinical progressive disease, or unmanageable toxicity, preferably up to 17 or more doses.

The growth inhibitory HER2 antibody preferably is trastuzumab, which typically is administered as an intravenous loading dose of about 8 mg/kg, followed by the administration of 6 mg/kg doses in subsequent cyclies. Trastuzumab is typically administered every 3 weeks until radiographic or clinical progressive diease or unmanageable toxicity, preferably up to 17 or more doses.

The taxane preferably is docetaxel, which is typically administered as an IV dose of 75 mg/m$^2$ every 3 weeks for at least 6 cycles until radiographic or clinical progressive disease or unmanageable toxicity.

The HER2 antibodies preferably are administered as naked antibodies. However, the inhibitor administered may be conjugated with a cytotoxic agent. Preferably, the conjugated inhibitor and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

In one embodiment, treatment starts with the administration of pertuzumab, or HER2 dimerization inhibitor antibody, followed by administration of trastuzumab or another growth inhibitory HER2 antibody and a taxane, e.g. docetaxel, on the following day. In another embodiment, treatment starts with trastuzumab, or another growth inhibitory HER2 antibody, followed by the administration of pertuzumab, or another HER2 dimerization inhibitor antibody, and a taxane, e.g. docetaxel. In yet another embodiment, all three agents are administered on the same day, in any order.

The dosages and treatment protocols described herein are for information purposes only, and can be altered by a skilled physician considering factors specific to the patient and cancer to be treated, such as the patient's age, weight, overall physical condition, treatment history, the severity and type of the breast cancer to be treated, the extent and nature of the metastasis, and the like.

VI. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

Further details of the invention are illustrated by the following non-limiting Examples. The disclosures of all citations in the specification are expressly incorporated herein by reference.

Glossary of Abbreviations

FACT-B Functional Assessment of Cancer Therapy-Breast
FFPE Formalin-fixed paraffin-embedded
FISH Fluorescence in situ hybridization
GGT Gamma-glutamyl transferase
ICH International Conference on harmonization
IHC Immunohistochemistry
ITT Intent to treat
IV Intravenous
JVP Jugular Venous Pressure
LDH Lactate dehydrogenase
LLN Lower limit of normal
MBC Metastatic breast cancer
MRI Magnetic resonance imaging
NCI-CTC National Cancer Institute Common Toxicity Criteria
NCI-CTCAE National Cancer Institute Common Terminology Criteria for Adverse Events
ORR Objective response rate
OS Overall survival
PD Progressive disease
PFS Progression-free survival
PK Pharmacokinetic
PR Partial response
PS Performance status
aRTT Activated partial thromboplastin time
RECIST Response Evaluation Criteria in Solid Tumors
SAE Serious adverse event
SD Stable disease
TOI-PFB Trial Outcome Index-Physician Function Breast
ULN Upper limit of normal

EXAMPLE 1

Phase III Clinical Study to Evaluate the Efficacy and Safety of Pertuzumab+Trastuzumab+Docetaxel Treatment of Previously Untreated Metastatic Breast Cancer Primary Objectives The primary objective of this study is to compare progression-free survival (PFS) based on tumor assessments by an independent review facility (IRF) between patients in two treatment arms:
placebo+trastuzumab+docetaxel vs. pertuzumab+trastuzumab+docetaxel.

Secondary Objectives
To compare overall survival (OS) between the two arms
To compare PFS between the two treatment arms based upon investigator assessment of progression
To compare the overall objective response rate between the two treatment arms
To compare the duration of objective response between thet two treatment arms
To compare the safety profile between the two treatment arms
To compare time to symptom progression, as assessed by the FACT Trial Outcome Index-Physical Functional Breast (TOI-PFB)
To evaluate if biomarkers from tumor tissues or blood samples (e.g., HER3 expression, Fcγ, and serum ECD/HER2 and/or HER ligands concentrations) correlate with clinical outcomes.

Target Population
The study enrolls 800 patients from approximately 250 sites worldwide. The study population is patients with HER2-positive metastatic breast cancer (MBC) who have not previously been treated with chemotherapy and/or biologic therapy for their MBC. Patients with Stage IV disease at initial disease presentation as well as those who have progressed following either neo-adjuvant or adjuvant therapy with a disease-free interval of at least 12 months are included, and they may have received trastuzumab and/or taxanes in the adjuvant setting.

Investigational Drug

The investigational drug is pertuzumab in combination with trastuzumab and docetaxel, compared to the administration of placebo in combination with trastuzumab and docetaxel.

Blinded Pertuzumab/Placebo

Pertuzumab/placebo are administered as an IV loading dose of 840 mg for Cycle I, and 420 mg for subsequent cyclies. Pertuzumab/placebo are administered every 3 weeks until investigator-assessed radiographic or clinical progressive disease, or unmanageable toxicity. Administration may be delayed to assess ot treat adverse events such as cardiac adverse events or mylosuppression. No dose reduction is allowed.

If the patient misses a dose of pertuzumab/placebo for 1 cycle (i.e., the 2 sequential administration times are 6 weeks or more apart), a re-loading dose of pertuzumab/placebo (840 mg) should be given. If re-loading is required for a given cycle, the 3 study therapies should be given on the same schedule as Cycle 1, i.e., pertuzumab/placebo on Day 1, and trastuzumab and docetaxel on Day 2. Subsequent maintenance pertuzumab doses of 420 mg are thn given every 3 weeks, starting 3 weeks later.

Because the pertuzumab/placebo formulation does not contain a preservative, the vial seal may only be punctured once. Any remaining solution should be discarded.

The indicated volume of pertuzumab/placebo solution should be withdrawn from the vials and added to a 250-cc IV bag of 0.9% sodium chloride injection.

Trastuzumab

Trastuzumab is administered as an IV loading does of 8 mg/kg for Cycle 1, and 6 mg/kg for subsequent cyclies. The dose of trastuzumab does not need to be recalculated unless the body weight has changed by more than ±10% from baseline.

Trastuzumab is administered every 3 weeks until investigator-assessed radiographic or clinical progressive disease, or unmanageable toxicity. Administration may be delayed to assessed ot treat adverse events such as cardiac adverse events or myelosuppression. No dose reduction is allowed.

If the patient misses a dose of trastuzumab for 1 cycle (i.e., the 2 sequential administration times are 6 weeks or more apart), a re-loading dose of pertuzumab/placebo (8 mg/kg) should be given. If re-loading is required for a given cycle, the 3 study therapies should be given on the same schedule as Cycle 1, i.e., pertuzumab/placebo on Day 1, and trastuzumab and docetaxel on Day 2. Subsequent maintenance trastuzumab doses of 6 mg/kg are thn given every 3 weeks, starting 3 weeks later.

For administration, each vial of trastuzumab 150 mg is reconstituted with 7.2 mL of Sterile Water for Injection (SWFI). This formulation does not contain a preservative and is suitable for single use only.

Each vial of trastuzumab 440 mg is reconstituted with 20 mL of either SWFI or Bacteriostatic Water for Injection (BWFI), USP, 1.1% benzyl alcohol preserved, as supplied. If the trastuzumab is reconstituted with SWFI, it is suitable for single use only.

The reconstituted solution contains 21 mg/mL of trastuzumab, at a pH of approximately 6.0, and the appropriate calculated volume will be added in to 250 mL of 0.9 Sodium Chloride Injection. The appropriate volume is calculated (in mL) using the following formula:

$$\text{Body Weight (in kg)} \times \text{Dose (8 mg/kg for loading or 6 mg/kg for maintenance)}/21 \text{ mg/mL (concentration of reconstituted solution).}$$

Docetaxel

Docetaxel is administered as an IV dose of 75 mg/m$^2$ every 3 weeks for at least 6 cycles until investigator-assessed radiographic or clinical progressive disease or unmanageable toxicity. At the discretion of the treating physician, the docetaxel dose is increased to 100 mg/m$^2$ for patients who tolerate at least 1 cycle without any of the following toxicitiesL febrile neurtopenia, Grade 4 neutropenia for >5 days or ANC<100/µL for more than 1 day, or other non-hematoloical toxicities of Grade>2 (NCI/CTCAE, Version 3). For further details, refer to docetaxel Package Insert.

Treatment Schedule

For the first cycle of treatment, blinded pertuzumab/placebo is given of Day 1 over 60 minutes followed by a 60-minute observation period. Trastuzumab and docetaxel is administered on Day 2 of Cycle I using the labeled guidelines for administration.

If the administrations of all three agents are well tolerated in Cycle 1, they may be given sequentially on Day 1 in subsequent cycles thereafter. If the subject cannot tolerate all three drugs given on the same day, the Cycle 1 dosing schedule (pertuzumab/placebo on Day 1, trastuzumab and docetaxel on Day 2) is followed.

If one ot both of the monoclonal antibody study drugs needs to be permanently discontinued or is held for more than two cycles, the subject is taken off the study treatment. However, if docetaxel needs to be permanently discontinued for reasons related to toxicity, the subject can continue on monoclonal antibody study drugs.

Inclusion Criteria

Disease-Specific Inclusion Criteria

1. Histologically or cytologically confirmed adenocarcinoma of the breast with locally recurrent or metastatic disease, and candidate for chemotherapy. Patients with measurable and nonmeasurable lesion are eligible.

Locally recurrent disease must not be amenable to resection with curative intent.

Note: Patients with de-novo Stage IV disease are eligible.

2. HER2-positive (defined as 3+IHC or FISH amplification ratio≥2.0) MBC confirmed by a Sponsor-designated central laboratory. It is strongly recommended that a formalin-fixed paraffin-embedded (FFPE) tissue block from the primary tumor be submitted for central laboratory confirmation of HER2 eligibility; however, if that is not possible, 25 unstained and freshly cut slides will be submitted. (Tissue will subsequently be used for assessment of biomarkers.)

General Inclusion Criteria:

3. Age≥18 years

4. Left Ventricular Ejection Fraction (LVEF)≥50% at baseline (within 42 days of randomization) as determined by either ECHO or MUGA (ECHO is the preferred method. If the patient is randomized, the same method of LVEF assessment, ECHO or MUGA, must be used throughout the study, and to the extent possible, be obtained at the same institution). All pre-study LVEF values during and post-trastuzumab adjuvant treatment for patients who received such adjuvant therapy prior to enrollment into the study will be collected.

5. Eastern Cooperative Oncology Group (ECOG) performance status (PS) 0 or 1

6. For women of childbearing potential, agreement to use an effective form of contraception (patient and/or partner, e.g., surgical sterilization, a reliable barrier method) and to continue its use for the duration of study treatment and for 6 months after the last dose of study treatment.

7. Signed, written informed consent (approved by the Institutional Review Board or Independent Ethics Committee) obtained prior to any study procedure.

Cancer-Related Exclusion Criteria

1. History of anticancer therapy for MBC (with the exception of one prior hormonal regimen for MBC). This includes any EGFR or anti-HER2 agents or vaccines, cytotoxic chemotherapy, or more than one prior hormonal regimen for MBC.

2. History of approved or investigative tyrosine kinase/HER inhibitors for breast cancer in any treatment setting, except trastuzumab used in the neoadjuvant or adjuvant setting 3. History of systemic breast cancer treatment in the neo-adjuvant or adjuvant setting with a disease-free interval from completion of the systemic treatment (excluding hormonal therapy) to metastatic diagnosis of <12 months.

4. History of persistent Grade≥2 hematologic toxicity resulting from previous adjuvant therapy.

5. Current peripheral neuropathy of NCI-CTCAE, Version 3.0, Grade≥3 at randomization.

6. History of other malignancy within the last 5 years, except for carcinoma in situ of the cervix or basal cell carcinoma.

7. Current clinical or radiographic evidence of central nervous system (CNS) metastases. CT or MRI scan of the brain is mandatory (within 28 days of randomization) in cases of clinical suspicion of brain metastases.

8. History of exposure to the following cumulative doses of anthracyclines:

doxorubicin or liposomal doxorubicin>360 mg/m2 epirubicin>720 mg/m2 mitoxantrone>120 mg/m2 and idarubicin>90 mg/m2

Other (e.g., liposomal doxorubicin or other anthracycline>the equivalent of 360 mg/m2 of doxorubicin)

If more than 1 anthracycline has been used, then the cumulative dose must not exceed the equivalent of 360 mg/m2 of doxorubicin.

Hematological, Biochemical, and Organ Function

9. Current uncontrolled hypertension (systolic>150 mmHg and/or diastolic>100 mmHg) or unstable angina 10. History of CHF of any New York Heart Association (NYHA) criteria, or serious cardiac arrhythmia requiring treatment (exception, atrial fibrillation, paroxysmal supraventricular tachycardia)

11. History of myocardial infarction within 6 months of randomization

12. History of LVEF decline to below 50% during or after prior trastuzumab neo-adjuvant or adjuvant therapy 13. Current dyspnea at rest due to complications of advanced malignancy, or other diseases that require continuous oxygen therapy.

General Exclusion Criteria

14. Inadequate organ function, evidenced by the following laboratory results within 28 days prior to randomization:

Absolute neutrophil count<1,500 cells/mm3

Platelet count<100,000 cells/mm3

Hemoglobin<9 g/dL

Total bilirubin>upper limit of normal (ULN) (unless the patient has documented Gilbert's syndrome)

AST (SGOT) and ALT (SGPT)>2.5×ULN

AST (SGOT) or ALT (SGPT)>1.5×ULN with concurrent serum alkaline phosphatase>2.5×ULN (unless bone metastases are present)

Serum creatinine>2.0 mg/dL or 177 μmol/L

International normalized ratio (INR) and activated partial thromboplastin time (aPTT)>1.5×ULN (unless on therapeutic coagulation)

15. Current severe, uncontrolled systemic disease (e.g., clinically significant cardiovascular, pulmonary, or metabolic disease; wound healing disorders; ulcers; or bone fractures)

16. Major surgical procedure or significant traumatic injury within 28 days prior to study treatment start or anticipation of the need for major surgery during the course of study treatment 17. Pregnant or lactating women 18. History of receiving any investigational treatment within 28 days of randomization 19. Current known infection with HIV, HBV, or HCV 20. Receipt of IV antibiotics for infection within 14 days of randomization 21. Current chronic daily treatment with corticosteroids (dose of >10 mg/day methylprednisolone equivalent) (excluding inhaled steroids)

22. Known hypersensitivity to any of the study drugs

23. Assessed by the investigator to be unable or unwilling to comply with the requirements of the protocol.

Assessments

Efficacy

The primary endpoint is PFS based on IRF evaluations. PFS is defined as the time from randomization to the first documented radiographical progressive disease, as determined by the IRF using current RECIST (Therasse et al. 2000), or death from any cause, whichever occurs first.

Carcinomatous meningitis diagnosed by cytologic evaluation of cerebral spinal fluid will also define progressive disease. Medical photography will also be allowed to monitor chest wall recurrences of subcutaneous lesions.

Overall survival is the key secondary endpoint, and is defined as the time from the date of randomization to the date of death from any cause.

Safety

Safety outcome measures are as follows:

Incidence of Symptomatic left ventricular systolic dysfunction [Congestive Heart Failure (CHF)] and asymptomatic left ventricular ejection fraction (LVEF) events LVEF measurements over the course of the study Incidence and severity of adverse events (AEs) and serious adverse events (SAEs)

Laboratory test abnormalities

Pharmacokinetics/QT (Substudy)

A subset of principal investigators and patients participates in a pharmacokinetic, drug-drug interaction, and QTc interval substudy as detailed in a separate protocol (see Example 2). Separate IRB/IEC approval and Informed Consent Form will be required for participation in the substudy.

Quality of Life/Pharmacoeconomics

Patient-Reported Outcomes Assessments: This study uses the Functional Assessment of Cancer Therapy-Breast (FACT-B), Version 4. The FACT-B has a 28-item generic score for all patients, plus nine items specific to breast cancer. Patients rate all items on a five-point scale ranging from "not at all" to "very much." The FACT-B provides supplemental domain valuative ratings or utility weights, thus providing an estimate of the relative importance of each quality of life domain to an individual patient. The FACT-B provides a total QoL score as well as information about physical well-being, social/family well-being, functional well-being, and disease-specific concerns. The FACT-B has been used extensively and has demonstrated reliability, validity, and sensitivity to change over time. Only female patients on this study will be asked to complete the FACT-B questionnaire.

Pharmacoeconomic Assessments

An economic assessment comparing various costs between the two treatment arms is conducted by evaluating hospitalizations while on study treatment. The number of hospital visits, number of days admitted, and type of visits (emergency room vs. inpatient care) will be collected. This information will be collected from information submitted on AE and SAE electronic case report forms (eCRFs).

Sample Collection

Archival tumor samples from the primary tumor (or metastatic sites, if the primary tumor is not available) are submitted from all subjects during screening and submitted to a central pathology laboratory for assessment of HER2 status via IHC and FISH for study eligibility, as well as for the assessment of tumor tissue biomarkers for pertuzumab/trastuzumab response prediction. Tumor tissue samples are submitted in the form of either paraffin blocks or unstained, freshly cut slides containing formalin-fixed tumor tissue. Because uncontrolled oxidation processes on the slides may affect slides, tumor tissue blocks are preferred. However, if a tumor block is not available, 25 unstained freshly cut slides of 4 μm are submitted (the number of slides submitted may be reduced pending on the regulatory and or IEC requirements of some counties). The slides must be sent to the central lab within 2 days of being cut. From submitted tumor blocks, at the central laboratory a maximum of 15 slides will be cut and 2 cores will be removed in order to construct tissue microarrays (TMAs) for later analysis. The remaining part of the tumor block will be returned to the institution. HER2 testing will be prioritized and the tissue will subsequently be used for assessment of biomarkers.

For the assessment of tumor tissue biomarkers, a variety of analysis methodologies may be used, including but not limited to, qRT-PCR, IHC, in-situ hybridization, and gene expression profiling. At the end of the collection process, the most suitable analytical methodologies will be selected and employed.

Tissue Microarray (TMA) Construction

The tumor blocks are also used to set up a TMA: a maximum of 2 tissue cores of 1.5 mm each are taken out using a puncher and then rearranged as an array into a block of wax. A single array may include tissue cores from different patients. This process protects the tissue against oxidation and allows for long-term storage and later analysis.

For later analysis, tissue sections can be generated using the latter tissue microarray. This technology allows a high throughput (many patient samples on one glass slide) analysis of biomarkers.

DNA/RNA Extraction

The submitted tumor blocks are used to generate sections on glass slides for the extraction of tumor DNA and RNA for later analysis. These slides are prepared in a central lab to ensure the same quality for all samples and in later studies. Note that as tumorigenesis is a multiple-step process linked to somatic events, DNA analysis will focus on sporadic mutations specifically found in tumor tissue but not inherited changes found in the whole body. For this purpose, some sections containing tumor will be taken from the block and used for the extraction process. The tumor tissue samples will be stored at the study Sponsors' facility or a contract laboratory facility for up to 7 years after database closure, at which time the samples will be destroyed.

Metastatic Tumor Tissue Samples for Biomarker Analysis (Optional)

If a biopsy of the patient's metastatic tumor tissue is available, it is submitted from consenting patients at baseline (after the patient has been determined to be eligible for the study, but before the first administration of study medication) for the assessment of tumor tissue biomarkers for pertuzumab/trastuzumab response prediction.

Serum Samples for ECD/HER2 and HER Ligands Analysis

For assessment of serum biomarkers that may indicate response to pertuzumab and trastuzumab, serum samples (from an approximately 5 mL blood draw) are collected at baseline (after the patient has been determined to be eligible for the study but before the first administration of study medication) and during the study at the time of each tumor assessment. Biomarker assessments with these samples will include levels of ECD/HER2, selected HER ligands, and/or markers thought to be important for HER family signaling or response to HER inhibitors and HER activation. Leftovers of samples may be used for re-testing or developing and validating existing and/or new diagnostic tests related to pertuzumab or trastuzumab, or both.

Whole Blood Sample for Fcγ Polymorphism Analysis (Clinical Genotyping)

A whole blood sample (3 mL) for assessment of Fcγ polymorphism is collected from patients at baseline (after the patient has been determined to be eligible for the study but before the first administration of study medication). An analysis of Fcγ-receptor polymorphism is correlated with clinical outcome in order to further evaluate the mechanism of action of both trastuzumab and pertuzumab. Mandatory blood collection for polymorphic analysis will be pending on the regulatory and or IEC requirements of the individual countries.

Serum and Plasma for Biomarker Sample Repository (BSR) Research (Optional)

Blood samples for extraction of serum and plasma samples (approximately 5 mL per sample) for biomarker discovery, validation, and application will be collected from consenting patients. These samples are collected at baseline (after the patient has been determined to be eligible for the study but before the first administration of study medication) and during the study every 9 weeks at the time of every tumor assessment until IRF-determined progressive disease. If IRF-determined PD occurs prior to post-treatment Week 18, BSR samples will continue to be collected every 9 weeks until posttreatment Week 18.

The collected BSR samples will be stored with the study Sponsor's facility or a contract laboratory facility for up to 15 years after the end of the associated study (database closure), at which time the samples will be destroyed. These samples will be used only for research purposes to identify dynamic biomarkers that may be predictive of response to pertuzumab and trastuzumab treatment (in terms of dose, safety, tolerability, and efficacy) and will help to better understand the pathogenesis, course, and outcome of breast cancer and related diseases and adverse events.

The collected blood samples may be used to develop and validate diagnostic assays and allow the generation of statistically meaningful biomarker data related to HER2-positive breast cancer disease or response to pertuzumab and/or trastuzumab. Since the identification of new markers that correlate with disease activity and the efficacy or safety of treatment is rapidly developing, the definitive list of analyses remains to be determined.

Study Duration

Patients remain in the treatment phase of the study until investigator-assessed radiographic or clinical progressive disease, unmanageable toxicity, or study termination by the Sponsors. Patients will not receive open-label pertuzumab after discontinuation from study treatment. After discontinuation of study treatment, tumor assessments will continue until IRF-assessed progression. In addition, patients will be followed for survival until death, loss to follow-up, withdrawal of consent, or study termination by the Sponsors. Tumor assessments will be conducted every 9 weeks from the date of randomization. Delays in treatment administration will not impact the timing of the tumor assessments. If a tumor assessment must be performed early/late, subsequent assessments will be conducted according to the original schedule of every 9 weeks from the date of randomization. Tumor assessments must be conducted until IRF-determined progressive disease (PD), even if treatment has been discontinued due to an investigator-determined PD or unacceptable toxicity.

After termination of study treatment, patients will continue be followed for survival until death, loss to follow-up, or study termination.

Sample Size

A sample size of 800 patients is needed to provide 80% power to detect a 33% improvement in OS (HR=0.75) at the two-sided significance level of 5%. Since both PFS and OS analyses are event-driven, and to avoid prolonged waiting period after final PFS analysis for OS data to reach the required number of events, the trial is designed to enroll sufficient number of patients such that approximately 50% of the required deaths will have been observed at the time of the final PFS analysis.

Assuming that the median OS in the control arm is 36 months and OS is exponentially distributed, one interim analysis at 50% of total requiredvdeaths, and a Lan-DeMets alpha-spending function with the O'Brien-Fleming stopping boundary, approximately 385 deaths will be required. In addition, assuming that the accrual rate is approximately 40 patients per month after a 9-month ramp-up period, v800 patients will need to be enrolled and followed for an additional 29.5 months to obtain 385 deaths. The enrollment period is estimated to be 26.5 months, and 50% of the required deaths will be reached at around 33.5 months.

Assuming that PFS is exponentially distributed with a median of 10.5 months in the control arm, it is estimated that 381 IRF-assessed PFS events, corresponding to approximately 448 investigator-assessed events, will have occurred when 50% of the required deaths (193 deaths) is reached. Final primary analysis of PFS will be performed after 381 IRF-assessed PFS events have occurred.

Statistical Methods

Efficacy Analyses

Analyses of PFS, OS, and time to symptom progression will be based on the intent-to-treat (ITT) population, defined as patients who have been randomized. For objective response, only patients with measurable disease at baseline will be included in the analysis. For duration of response, only responders will be included in the analysis. All efficacy analyses will be based on the treatment arm to which patients were randomized.

Analysis of Primary Variable

The primary endpoint is PFS based on IRF assessments. For patients who discontinue study treatment due to reasons other than death or IRF-assessed progression, every effort will be made to continue tumor assessments until IRF-determined progressive disease or patient death. Data for patients who do not have documented progressive disease or who have not died within 18 weeks of the last tumor assessment will be censored at the time of the last IRF-evaluable tumor assessment (or, if no tumor assessments are performed after the baseline visit, at the time of randomization plus 1 day).

For patients whose IRF-determined progression event is not available, surrogating death at any time as a progressive event can artificially prolong the PFS time because of a much longer life expectancy in this patient population compared with PFS. Therefore, only deaths within 18 weeks of the last tumor assessments will be included as an event in the primary analysis. However, a sensitivity analysis will be performed including all deaths as an event.

The log-rank test, stratified by prior treatment status (de novo and prior adjuvant or neo-adjuvant therapy) and region (Europe, North America, South America, and Asia), will be used to compare PFS between the two treatment arms. The unstratified log-rank test results will also be provided as a sensitivity analysis. The Kaplan-Meier approach will be used to estimate median PFS for each treatment arm. The Cox proportional hazard model, stratified by prior treatment status and region, will be used to estimate the HR between the two treatment arms (i.e., the magnitude of treatment effect) and its 95% confidence interval (CI).

The aforementioned analyses will be performed in demographic subgroups as appropriate. For example analysis may be performed in patient subgroups based on racial origin provided there is a reasonable sample size in the subgroups of interest.

Secondary Variables

Overall survival. Patients who are alive or lost to follow-up at the time of the analysis will be censored at the last known alive date. Patients with no post-baseline information will be censored at the time of randomization plus 1 day. Analysis methods are the same as those described for the primary endpoint. To minimize the chance of a biased OS estimate resulting from scheduled survival follow-up every 18 weeks, immediately prior to the data cutoff for the final PFS analysis and final OS analysis, the investigative sites will contact every patient that is alive to confirm current survival status. (The study Sponsors will notify all investigators of the timing of this survival data sweep.)

PFS based on investigator assessments. Data for patients who do not have documented progressive disease or who have not died within 18 weeks of the last tumor assessment will be censored at the time of the last investigator tumor assessment (or, if no tumor assessments are performed after the baseline visit, at the time of randomization plus 1 day). Analysis methods are the same as those described for the primary endpoint.

Objective response. Only patients with measurable disease at baseline will be included in the analysis of the objective response. Patients without a post-baseline tumor assessment will be considered to be non-responders. Analysis of objective response will be based on IRF assessments.

An estimate of the objective response rate and its 95% CI will be calculated for each treatment arm. The difference in objective response rate will also be provided with 95% CIs. The Mantel-Haenszel $\chi 2$ test stratified by prior treatment status and region will be used to compare the objective response rate between the two treatment arms. An unadjusted Fisher's exact test result will also be provided as a sensitivity analysis.

Duration of objective response. Only patients with an objective response will be included in the analysis of duration of objective response. The method for handling censoring is the same as that described for the primary endpoint. Analysis of duration of objective response will be based on IRF assessments.

Median duration of objective response for each arm will be estimated using the Kaplan-Meier approach. The hazard ratio between the two arms will also be estimated using Cox regression.

Time to symptom progression. A decrease of five points in TOI-PFB is considered symptom progression. Data for patients who do not have an observed symptom progression will be censored at the last observed TOI-PFB assessment date. If baseline TOI-PFB assessment is unavailable, or if there is no post-baseline TOI-PFB assessment performed, data will be censored at the time of randomization plus 1 day. Analysis methods are the same as those described for the primary endpoint.

Biomarker analyses. To evaluate the effect of molecular markers on efficacy outcome, efficacy outcomes will be summarized for all patients, and by treatment arm, within each subgroup determined by exploratory markers. Markers to be considered include the status of HER receptors, HER ligands, Fc-γ, shed antigens (e.g., ECD/HER2), and other markers relevant for the HER family pathway. Special emphasis will be put on markers that have shown association with clinical outcome in patients treated with pertuzumab in previous studies:

qRT-PCR markers: tumor gene expression profiles associated with HER2 activation

Baseline serum markers: levels of ECD/HER2 and HER ligands

Efficacy outcomes considered for this analysis will include PFS, objective response rate, and OS. The PFS and objective response will be based on the IRF assessments.

The biomarker analyses at the time of protocol development do not take the form of testing fixed hypotheses involving specific cutoffs or other pre-specified prediction rules. It is planned for the Statistical Analysis Plan (to be generated prior to unblinding of this trial) to use all available scientific evidence from independent studies or publications to specify testable prediction rules. In addition, this plan will specify in due detail how data-adaptive prediction rules will be derived (e.g., systematic cutoff search) and how the inherent multiplicity/bias will be corrected in order to prevent biased conclusions.

The difference in treatment benefit across biomarker statuses defined by a suitable prediction rule will be evaluated by testing the interaction effect of treatment and the prediction status using Cox regression for PFS and OS, and using logistic regression for response rate. These models involving an interaction term will also be used to estimate the conditional efficacy outcomes, conditional on biomarker prediction status or treatment arm, including and excluding the stratification factors into the model.

Clinical covariates can be of prognostic value and could interact with treatment benefit and with biomarker status. Candidates here are baseline variables of prognostic value describing tumour properties and morbidity status or common lab values. Biomarker prediction will be checked involving relevant clinical covariates, which could be part of the biomarker prediction function, if necessary.

Safety Analyses

The safety of pertuzumab in combination with trastuzumab and chemotherapy will be assessed through summaries of AEs, cardiac-specific AEs, LVEF measurements, and laboratory test results. Patients who receive any amount of study treatment will be included in safety analyses. Safety results will be summarized by the treatment patients actually receive.

EXAMPLE 2

Pharmacokinetic, Drug-Drug Interaction, and QTc Interval Substudy

This substudy has two main goals: (1) to describe the potential effects of pertuzumab on the QTc interval, and (2) to evaluate the pharmacokinetic profile of pertuzumab in the presence of trastuzumab and docetaxel and to describe any drug-drug interactions that might be observed when all three drugs are co-administered.

QTC Prolongation

Drug-induced prolongation of the QT/corrected QT (QTc) interval resulting in increased susceptibility to cardiac arrhythmia is a recognized complication of many drugs across a wide therapeutic spectrum (Morissette et al. *Can J Cardiol* 2005; 21:857-64). Prolongation of the QT/QTc interval, which is usually asymptomatic, may be manifested by syncope resulting from cardiac arrhythmias such as torsades de pointes (TdP), ventricular arrhythmia, and sudden cardiac death (Morganroth *rnst Schering Res Found Workshop* 2007; 59:171-84).

Measurement of QT is made by an electrocardiogram (ECG) and is a surrogate for ventricular repolarization. The QT interval is defined as the time from the beginning of the QRS complex to the end of the T-wave. Because the QT interval is inversely related to the heart rate, the following formulae are commonly used to correct the QT interval (Strevel et al. *J Clin Oncol* 2007; 25:3362-71).

Fridericia's Correction (QTcF): $QTcF=QT/RR^{0.33}$

Bazett's Correction (QTcB): $QTcB=QT/RR^{0.5}$

QTc is considered prolonged when it is greater than 450 milliseconds (ms) in duration. The QT/QTc interval can be affected by the location of the ECG lead, gender, time of day, drug therapy, or congenital conditions. Several pre-disposing factors may influence drug-induced arrhythmia secondary to prolonged QT/QTc, including electrolyte imbalance, bradycardia, toxins, cerebrovascular disease, inhibition of cytochrome p450, and inhibition of p-glycoprotein (Kannankeril and Roden *Curr Opin Cardiol* 2007; 22:39-43, Morissette et al 2005, supra).

The common mechanism of drug-induced QT/QTc interval prolongation is the direct blockade of specific potassium channels, encoded by the human ether-a-go-go (hERG)-related gene, that regulate cardiac repolarization or disrupt hERG channel protein trafficking, or both. Drugs have been classified by their propensity to prolong the QTc interval; the classification provided in Table 2 is commonly used (Woosley http//www.arizonacert.org (updated as of Mar. 1, 2006). To date, the drugs known to block potassium channels are small molecules, such as antiarrhythmics, some antibiotics, antiemetics, antihistamines, antipsychotics, antidepressants, bronchodilators, and some central nervous system (CNS) stimulants (Morissette et al. 2005m supra, Woosley 2006, supra). The binding site for potassium channel blockade is located on an intracellular domain, a site that is difficult for large molecules (i.e., monoclonal antibodies) to access.

Classes of molecularly-targeted oncology therapeutic agents associated with effects on the QT interval have been identified, including farnesyl protein transferase inhibitors, arsenic, Scr/Abl kinase inhibitors, multi-targeted tyrosine kinase inhibitors, histone deacetylase inhibitors, vascular disruption agents, and protein kinase C inhibitors. A direct mechanism common to these agents in association with QT effects has not been described (Streval et al. *J Clin Oncol* 2007; 25:3362-71).

TABLE 2

Classification of Drugs by Propensity to Prolong QTc Interval

| | |
|---|---|
| Drug List 1 | Generally accepted by authorities to have a risk of causing torsades de pointes |
| Drug List 2 | Drugs that in some reports may be associated with torsades de pointes but at this time lack substantial evidence for causing torsades de pointes |
| Drug List 3 | Drugs to be avoided for use in patients with diagnosed or suspected congenital long QT syndrome. Drugs on Lists 1, 2, and 4 should also be avoided by patients with QT syndrome |
| Drug List 4 | Drugs that, in some reports, have been weakly associated with torsades de pointes, and/or QT prolongation but that are unlikely to be a risk for torsades de pointes when used in the usual recommended dosages and in patients with out other risk factors (e.g., concomitant QT prolonging drugs, bradycardia, electrolyte disturbances, congenital long QT syndrome, concomitant drugs that inhibit metabolism) |
| Females > Males | Substantial evidence indicates a greater risk (usually > 2 fold) of torsades de pointes in women |

Pertuzumab Mechanism of Action and Nonclinical Experience

As described earlier, pertuzumab is a humanized monoclonal antibody based on human IgG1 (κ) framework sequences and consists of two heavy chains (449 residues) and two light chains (214 residues). Like trastuzumab (Herceptin®), pertuzumab is produced in Chinese hamster ovary (CHO) cells and is directed against HER2. However, it differs from trastuzumab in the epitope-binding regions of the light chain (12 amino acid differences) and heavy chain (29 amino acid differences). As a result, pertuzumab binds to a different epitope on HER2.

Pertuzumab acts by blocking the association of HER2 with other HER family members, including HER1 (EGFR), HER3, and HER4. As a result, it inhibits ligand-initiated intracellular signaling through two major signal pathways, MAP kinase and PI3 kinase. Inhibition of these signaling pathways can result in growth arrest and apoptosis, respectively (Hanahan and Weinberg *Cell* 2000; 100:57-70). Nonclinical data have demonstrated that overexpression of HER2 is not required for the anti-tumor activity of pertuzumab.

Proarrhythmias secondary to abnormal ventricular repolarization and QT prolongation have been of concern in drug development. Two International Conference on Harmonization (ICH) guidelines for nonclinical (S7B) and clinical (E14) testing were recently developed (International Conference on Harmonization of Technical Requirements for Registration of Pharmaceuticals for Human Use 2005). Based on these guidelines, the effect of pertuzumab on QTc in patients with breast cancer will be investigated in this substudy.

In order to fully characterize any potential effects of pertuzumab on the heart, additional cardiac endpoints have been included in two nonclinical multi-dose toxicology studies performed to support the clinical development of pertuzumab. In a 7-week intravenous toxicity and toxicokinetic study in cynomolgus monkeys with a 4-week recovery period (Study 00-377-1821), telemetry was measured in two animals per sex in the control and high-dose (150 mg/kg/dose) groups to collect electrocardiographic endpoints. At two timepoints before the initiation of treatment, and on Days 1 and 28, telemetered animals had systolic, diastolic, and mean arterial blood pressure, heart rate, PR interval, QRS, QT, and Lead II ECG data recorded. Four 1-minute tracings were collected for each animal from 2 to 22 hours after dosing and interpreted by a board-certified veterinary cardiologist. In addition to the routine serum chemistry parameters evaluated, serum was also analyzed for creatinine kinase isozymes and Troponin T on Study Days 2/3 and 44/45 for all animals. In a 26-week intravenous toxicity and toxicokinetic study with pertuzumab in cynomolgus monkeys with an 8-week recovery period (Study 01-458-1821), ECG (standard surface leads) and blood pressure measurements were recorded on all animals. Recordings were taken at two timepoints before the initiation of treatment and once during Weeks 4, 16, and 26 on anesthetized animals and were interpreted by a board-certified veterinary cardiologist. In addition to the routine serum chemistry parameters evaluated, serum was also analyzed for Troponin T on Day 1 predose and on Days 114, 184, and 239 (recovery) for all animals. Results from both multidose toxicity studies concluded that there was no evidence of cardiac injury caused by pertuzumab treatment, as determined by histopathology, lack of increases in relevant serum chemistry parameters (Troponin T and creatine kinase isozymes), and normal ECGs, blood pressures, and heart rates.

In clinical trials as of November 2006, there has been no association noted of an increase of TdP in pertuzumab-treated patients.

Pertuzumab Pharmacokinetics

Summary

Pharmacokinetic (PK) results observed in previous pertuzumab studies showed no change in clearance at doses from 2.0 to 15.0 mg/kg (140 mg-1050 mg for a 70 kg patient). A two-compartment model adequately described the concentration-time data, with a systemic serum clearance of approximately 0.24 L/day and a terminal half-life of approximately 17 days for a typical patient. Based on these data, a dosing interval of 3 weeks is recommended in clinical studies. In Phase II studies, a loading dose of 840 mg (followed by 420 mg every 3 weeks), led to the attainment of steady-state trough ($C_{min}$) and peak ($C_{max}$) concentrations by the second cycle and achieved a PK target of 20 µg/mL (based on pre-clinical tumor xenograft models). Population PK modeling of data from Phase Ia and Phase II studies support the continued use of fixed, nonweight-based dosing in female patients. There was no evidence that pertuzumab impacted the PK of co-administered chemotherapeutic agents (docetaxel and cape citabine in Phase Ib studies and gemcitabine in a Phase II study).

Pharmacokinetics in Single-Agent Studies

Figure 6:
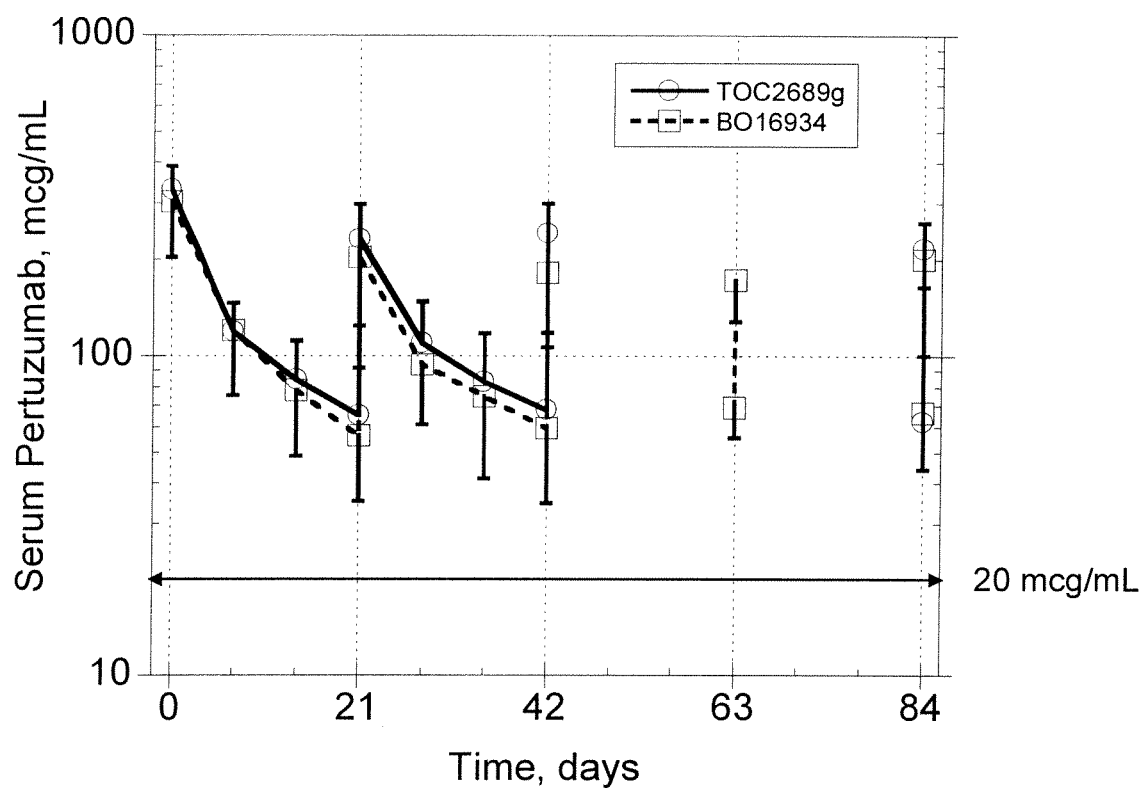
FIG. 6. Serum Pertuzumab Concentrations (μg/mL) for the First 84 Days (through Study Day 85) for Studies TOC2689g and BO16934.

In Phase II single-agent studies (Studies TOC2689g and BO16934), concentration-time data show that the loading dose 840 mg (followed by 420 mg every 3 weeks) resulted in the achievement of steady-state $C_{min}$ and $C_{max}$ by the second cycle, and also achieved serum pertuzumab target concentrations >20 µg/mL in most patients. Mean serum $C_{min}$ and $C_{max}$ for the first two cycles of treatment in ovarian and metastatic breast cancer (MBC) patients are presented in Table 3. FIG. 6 shows the concentration-time profiles for the first 84 days.

TABLE 3

Mean (±SD) Peak and Trough Serum Concentrations at the End of the First and Second Treatment Cycles (Studies TOC2689g and BO16934)

| Study | Dose | Cycle 1 | | Cycle 2 | |
|---|---|---|---|---|---|
| | | $C_{min}$ µg/mL | $C_{max}$ µg/mL | $C_{min}$ µg/mL | $C_{max}$ µg/mL |
| TOC2689g Ovarian cancer | 420 mg (n = 61) | 64.6 (±20.9) | 231.7 (±50.6) | 66.5 (±38.0) | 237.6 (±55.0) |
| | 1050 mg (n = 62) | 90.1 (±68.1) | 390.9 (±114.7) | 94.7 (±47.3) | 357.2 (±112.4) |
| BO16934 Metastatic breast cancer | 420 mg (n = 40) | 56.5 (±21.2) | 202.9 (±78.4) | 62.6 (±21.1) | 181.2 (±63.0) |
| | 1050 mg (n = 35) | 75.9 (±34.5) | 425.6 (±166.9) | 136.6 (±53.5) | 542.9 (±173.7) |

PK parameters were estimated using a two-compartment model (see Table 4). The mean systemic clearance for these patients (0.225-0.285 L/day), and the mean volume of distribution of the central compartment (2.70-3.11 L; i.e., approximately the serum volume), were similar to that observed in the Phase Ia study (Study TOC2297g). The mean initial half-life and the mean terminal half-life were also within the ranges observed across 2-15 mg/kg dose groups in the Phase Ia study.

TABLE 4

Estimates[a] of Selected Pertuzumab Pharmacokinetic Parameters following Intravenous Infusion (Mean ± SD)[b]

| Study | Dose Group | CL (L/day) | $V_c$ (L) | $V_{ss}$ (L) | $t_{1/2}$ initial (days) | $t_{1/2}$ terminal (days) |
|---|---|---|---|---|---|---|
| TOC2689g (Ovarian cancer) | 420 mg (n = 61) | 0.244 ± 0.095 | 2.70 ± 0.39 | 4.73 ± 0.78 | 1.37 ± 0.12 | 16.2 ± 4.7 |
| | 1050 mg (n = 62) | 0.285 ± 0.119 | 3.11 ± 0.72 | 5.39 ± 1.31 | 1.34 ± 0.11 | 15.8 ± 5.2 |
| BO16934 (Metastatic breast cancer) | 420 mg (n = 40) | 0.255 ± 0.096 | 2.98 ± 0.67 | 5.12 ± 0.98 | 1.36 ± 0.13 | 16.3 ± 3.5 |
| | 1050 mg (n = 35) | 0.225 ± 0.121 | 2.95 ± 0.81 | 5.11 ± 1.12 | 1.39 ± 0.15 | 20.5 ± 8.1 |

CL = systemic clearance;
$V_c$ = volume of central compartment;
$V_{ss}$ = steady-state volume of distribution;
$t_{1/2}$ initial = initial distribution half-life;
$t_{1/2}$ terminal = terminal half-life
[a]Pharmacokinetic parameters estimated by post-hoc analysis from 2-compartment population pharmacokinetic model.
[b]Pharmacokinetics not performed for Study TOC2572g.

Pharmacokinetics in Combination Therapy Studies

Analyses of the PK data from Phase Ib studies of capecitabine (Study BO17003) and docetaxel (Study BO17021) indicate that pertuzumab does not alter the PK of these two cytotoxic agents. In both studies, the PK parameters for pertuzumab were similar to the PK parameters obtained in single-agent pertuzumab studies.

Preliminary PK analysis from a Phase II study to evaluate the efficacy of pertuzumab in combination with gemcitabine in patients with platinum-resistant ovarian cancer (Study TOC3258g) indicates that pertuzumab does not alter the PK of gemcitabine or its major metabolite, dFdU. In addition, the serum concentrations of pertuzumab were similar to the concentrations in the single-agent Phase II studies in ovarian cancer and MBC (Studies TOC2689g and BO16934)

Pertuzumab Dose Regimen

A dosing regimen of pertuzumab administered every 3 weeks to patients in Phase II studies (Studies TOC2689g and BO016934) using a fixed 840 mg loading dose (equivalent to 12 mg/kg for a 70 kg patient) for treatment Cycle 1 and a fixed 420 mg maintenance dose (equivalent to 6 mg/kg for a 70 kg patient) for subsequent treatment cycles resulted in steady-state serum $C_{min}$ of approximately 60 µg/mL by the second treatment cycle. In nonclinical dose-response xenograft studies using nude mice implanted with nonsmall cell lung cancer (NSCLC) and breast cancer tumors (low and high HER2 expression levels), >80% suppression of tumor growth was achieved when steady-state trough concentrations of pertuzumab reached 5-25 µg/mL. Thus, the steady-state $C_{min}$ that were observed in patients in the Phase II studies are in excess of concentrations shown to be efficacious in animal tumor models, and therefore expected to result in a biologic effect.

A preliminary population PK analysis of the Phase Ia (Study TOC2297g) and Phase IIa studies (Studies TOC2689g and BO16934), comprising a total of 153 patients (weight range: 45.0-150.6 kg) and 1458 concentration-timepoints, showed that the population variability of steady-state trough concentration and exposure were similar with fixed-dosing, body surface area-based dosing, and weight-based dosing. Therefore, a dose based on body-surface area or weight was not superior to a fixed dose. These data support the continued use of a fixed dose of pertuzumab in female patients with MBC and ovarian cancer.

The dependence of pertuzumab serum clearance on body weight for both female and male patients will be evaluated further using all available clinical PK data from the pertuzumab studies.

Objectives

Pharmacokinetic Objectives

The PK objectives of this substudy are the following:

To characterize the pharmacokinetics of pertuzumab in patients with HER2-positive MBC, and to compare these data with PK data from other clinical studies.

To characterize the potential of a drug-drug interaction of pertuzumab on the pharmacokinetics of docetaxel (in the presence of trastuzumab), and on the pharmacokinetics of trastuzumab (in the presence of docetaxel).

Electrocardiogram Objectives

The ECG objectives are exploratory and may include the following:

To describe the effect of pertuzumab on the change from baseline in QTc interval as calculated using Fridericia's correction (QTcF)

To describe the effect of pertuzumab on the change from baseline in QTc interval as calculated using Bazett's correction (QTcB)

To describe the proportion of patients with QTc interval prolongation and change from baseline in QTc interval, calculated using both the Fridericia's and Bazett's corrections To describe the effect of pertuzumab on the following ECG parameters: heart rate, QT interval, PR interval, and QRS duration Study Design Description of the Study This is a supplemental study to Study TOC4129g/WO20698 that is designed to evaluate the effect of pertuzumab on QTc interval, further evaluate the pharmacokinetics of pertuzumab, and characterize the drug-drug interaction of pertuzumab on docetaxel pharmacokinetics (in the presence of trastuzumab), and on trastuzumab pharmacokinetics (in the presence of docetaxel).

A subset of investigative sites participating in Study TOC4129g/WO20698 will participate in this substudy. Patients at these sites who have consented to participate in and have been determined to be eligible for enrollment into Study TOC4129g/WO20698 will be invited to participate in this substudy. Participation in this substudy is optional; therefore, informed consent for this substudy will be obtained separately from the consent to participate in Study TOC4129g/WO20698. Refusal to participate in this substudy will not affect a patient's eligibility a patient's eligibility for Study TOC4129g/WO20698. Fifty evaluable patients (25 per treatment arm) will be enrolled to this substudy.

Each enrolled patient will receive treatment as specified in TOC4129g/WO20698. Day 1 of TOC4129g/WO20698 will correspond to Day 1 of this substudy.

All patients participating in this substudy will have alpha-1-acid glycoprotein tested at baseline by a local laboratory, in addition to the standard hematology and serum chemistry tests in Study TOC4129g/WO20698.

Triplicate 12-lead ECG measurements will be taken during the pre-treatment baseline period from Day −7 to Day −1 (i.e., within 7 days prior to Cycle 1 Day 1), at Cycle 1 Day 1, at Cycle 1 Day 3, coincident with the 23-hour docetaxel PK sample, and at Cycle 3 Day 1 (corresponding to pertuzumab/placebo steady-state $C_{min}$ and $C_{max}$). On Day 1 of Cycle 1 and Cycle 3, triplicate 12-lead ECG measurements will be taken at the following timepoints: −30 and −15 minutes pre-pertuzumab/placebo infusion (any premedication that is required before the pertuzumab/placebo infusion must be given between these two pre-dose timepoints), immediately post-pertuzumab/placebo infusion, and 60-75 minutes post-pertuzumab/placebo infusion. ECG results will be sent to a central core cardiology laboratory for the determination of the QT/QTc interval, which will be used as the data for this substudy.

To minimize variations due to circadian rhythms, the Cycle 1 and Cycle 3 pertuzumab/placebo infusions should be administered at the same time of day, and the baseline (Day −7 to Day −1) ECG readings must be taken at the same corresponding time of day as the Cycle 1 and Cycle 3 ECG measurements. The severity of QTc prolongation will be graded according to the National Cancer Institute Common Toxicity Criteria for Adverse Events (NCI-CTCAE), Version 3.0. A treatment algorithm is provided to guide study treatment decisions based upon the observed QT/QTc interval at each timepoint. If at any time during this substudy the QTc interval exceeds 500 ms or a high degree of artifact is present on the ECG, cardiac consultation with the ECG core laboratory is available.

Blood samples for pertuzumab PK evaluation will be drawn before and after the pertuzumab/placebo infusions at Cycles 1, 3, 6, 9, 12, 15, 18, with an additional sample drawn at the Treatment Discontinuation Visit (28-42 days after the last dose of study treatment). At Cycles 1 and 3, the post-pertuzumab PK samples will be drawn 60-75 minutes after the end of the pertuzumab/placebo infusion to correspond with the ECGs performed on those days.

Blood samples for trastuzumab PK evaluation will be collected at Cycles 1 and 3, before and after the trastuzumab infusions.

Blood samples for the docetaxel PK evaluation will be collected at Cycle 1 at the following timepoints after the initiation of docetaxel infusion (Timepoint 0): 0.5 hour (during infusion), 1.0 hour (at the end of infusion, EOI), 1.25 hours (15 minutes after the EOI), 2 hours (1 hour after EOI), 4 hours (3 hours after EOI), 6 hours (5 hours after EOI), 8 hours (7 hours after EOI), and 24 hours (Cycle 1 Day 3, 23 hours after EOI).

Rationale for Study Design

Rationale for QTc Study Design

The study will evaluate the effect of pertuzumab on the QTc interval in patients with HER2-positive MBC. Ordinarily, a thorough QTc study is performed in healthy volunteers when feasible. Because the QTc is to be evaluated in a cancer population with multiple confounders (baseline illness, baseline medications, including antiemetics, antibiotics, and other supportive care medications), this substudy has been designed to describe the change in QTc interval from baseline to steady-state in pertuzumab-treated and placebo control patients. If patients require antiemetics or other premedications prior to the infusion of pertuzumab/placebo, they must be given between the two pre-dose ECG measurements in an attempt to control for concomitant medication effects on the QT/QTc interval. ICH guidance recommends that studies should characterize the effect of a drug on the QT/QTc and perform ECG recordings at timepoints around the C.

As stated in the ICH E14 guidance, Bazett's correction generally over-corrects at elevated heart rates and under-corrects at heart rates below 60 beats per minute (bpm). Fridericia's correction has been chosen as the primary correction because it accounts for the effect of altered heart rates on QT interval.

Pertuzumab PK samples will be drawn at the time of the Cycles 1 and 3 ECG readings when therapeutic serum concentrations of pertuzumab are expected to be achieved. Pertuzumab exposure will be correlated with QTc. Cycle 3 Day 1 (assuming 21-day cycles) was chosen for the measurement of QTc at steady-state concentration based on the Phase II studies, during which a loading dose of 840 mg (followed by 420 mg every 3 weeks) resulted in the achievement of steady-state $C_{min}$ and $C_{max}$ by the second cycle. Therefore, the majority of the population should be at steady state by Cycle 3.

Although a positive-control comparison drug (e.g., moxifloxacin) is recommended by ICH guidelines to validate assay sensitivity, a positive control drug will not be administered to patients in this substudy as it is felt that the use of a positivecontrol medication would not be ethical in a metastatic cancer patient population. Furthermore, patients have baseline variability secondary to medications already being administered.

Per ICH recommendations, rates of selected adverse events, if observed (TdP; sudden death; ventricular tachycardia; ventricular fibrillation and flutter; syncope; and seizures) will be compared between the pertuzumab-treated and control patients, as part of data collected for Study TOC4129g/WO20698. Additionally, the incidence of QTc interval prolongation and the change from baseline in QTc interval will be summarized.

Rationale for Pharmacokinetic Sampling

The proposed sampling scheme for pertuzumab concentration assessments in this substudy should allow for the adequate characterization of the pharmacokinetics of pertuzumab. The pertuzumab concentration results will be compared with available data from other pertuzumab clinical studies. In addition, the pertuzumab concentration data will be used for population PK modeling to generate PK parameter estimates. These data may also contribute to a future population PK analysis to investigate the effect of physiologic and disease-related covariates on PK parameters.

Study TOC4129g/WO20698 proposes to combine pertuzumab with trastuzumab and docetaxel. Based on the clearance mechanisms for pertuzumab, there is no expectation that pertuzumab will alter the pharmacokinetics of docetaxel. However, the concentrations of docetaxel will be measured to assess a potential PK-related interaction between docetaxel and pertuzumab (in the presence of trastuzumab). In addition, concentrations of trastuzumab will be measured to assess a potential PK-related interaction between trastuzumab and pertuzumab (in the presence of docetaxel).

Dose-ranging pharmacokinetics will not be performed, and a supratherapeutic dose will not be administered in Study TOC4129g/WO20698.

Outcome Measures

Pharmacokinetic Outcome Measures: The PK outcome measures are the following:

Observed minimum and maximum pertuzumab serum concentrations ($C_{min}$ and $C_{max}$), and PK parameter estimates (CL, AUC, Vd, $t_{1/2}$)

Minimum and maximum trastuzumab serum concentrations ($C_{min}$ and $C_{max}$)

Area-under-the-curve (AUC) for docetaxel plasma concentrations Electrocardiogram Outcome Measures: The ECG outcome measures are the following:

Time-matched baseline-adjusted placebo-corrected QTcF

Time-matched baseline-adjusted placebo-corrected QTcB

Proportion of patients at each timepoint whose ECG recordings meet the following criteria:

New incidence of absolute QTc interval prolongation (based on Fridericia's correction) of >450 ms, >470 ms, and >500 ms The following changes from baseline in QTc interval (based on Fridericia's correction): QTc increases>30 ms, QTc increases>60 ms Change from baseline in heart rate of ≥25%, resulting in a final heart rate <50 beats per minute (bpm) or >120 bpm New incidence of abnormal U waves New incidence of abnormal T waves New incidence of abnormal ECG morphology The time-matched baseline-adjusted placebo-corrected differences in the following ECG parameters: heart rate, QT, PR interval, and QRS duration.

Safety Plan

Clinically significant ECG changes detected during this substudy will be reported and managed according to the safety reporting and monitoring requirements of Study TOC4129g/WO20698. The degree of QTc prolongation will be graded according to the NCI-CTCAE, Version 3.0. A treatment algorithm is provided to guide study treatment decisions in the event of QT/QTc prolongation during the study. A central ECG core laboratory will be available to evaluate any cases of QT/QTc prolongation.

Control Group

Because Study TOC4129g/WO20698 is a randomized, double-blind, placebo-controlled study, the control group will consist of patients randomized to receive placebo instead of pertuzumab.

Minimization of Bias

For purposes of the main study, unblinding procedures will be performed according to the TOC4129g/WO20698 protocol. For this substudy, patient treatment (pertuzumab vs. control) will be determined by the analysis of PK serum samples for the presence or absence of pertuzumab; therefore, to maintain blinding of the main study, Sponsor personnel involved in the analysis of pertuzumab PK samples and analysis of this substudy will not be involved with any of the operational or analysis aspects of the Study TOC4129g/WO20698. All study personnel involved in the main TOC4129g/WO20698 study will remain blinded (e.g., site personnel, investigators, patients, statisticians, etc.).

Centralized ECG readers will be blinded to patient treatment and ECG timepoint.

Patients

Patient Selection

Patients who have consented to participate in Study TOC4129g/WO20698 at a subset of investigative sites will be eligible for enrollment into this substudy.

Inclusion Criteria: Patients must meet the following criteria to be eligible for substudy entry:

Enrollment in Study TOC4129g/WO20698

Signed Informed Consent Form for this substudy

Exclusion Criteria: Patients who meet any of the following criteria will be excluded from substudy entry:

Implantable pacemaker or automatic implantable cardioverter defibrillator (AICD)

Congenital long QT syndrome

Family history of long QT syndrome

Baseline QTc>450 ms as assessed locally at each study site

Patients currently requiring regular use of medications that are known to prolong QTc interval or induce TdP (see Appendix B)

Clinically significant bradycardia (defined as <50 bpm) at baseline

Evidence of heart block

Hypokalemia, hypomagnesemia, and hypocalcemia that cannot be corrected with electrolyte supplement Method of Treatment Assignment and Blinding Treatment assignment will be in accordance with the protocol described in Example 1.

Unblinding of study treatment will be in accordance with the procedures specified in Example 1. Centralized ECG readers will remain blinded to patient treatment and ECG timepoints.

Study Treatment

Study treatment will be as specified in Example 1.

Concomitant and Excluded Therapies

Clinical judgment should be applied when determining treatment options and supportive care treatment for each patient.

Other concomitant and excluded medications will be as directed in Example 1.

Study Assessments

Study treatment infusions, ECG measurements, and blood draws should be consistently administered, recorded, and collected at the same time of day, between 9:00 AM-12:00 PM and >1 hour postprandial, in order to minimize variations due to circadian rhythms.

Screening and Pretreatment Assessments

Informed consent must be obtained before study-specific evaluations are performed. The informed consent process should be documented in the patient's medical chart.

The following substudy evaluations and procedures will be performed during the baseline period of the study described in Example 1:

Written informed consent
Review of inclusion and exclusion criteria
Serum chemistry to evaluate electrolyte values
Collection of blood sample for alpha-1-acid glycoprotein test and analysis by a local laboratory, as an addition to the standard hematology and chemistry testing in the study described in Example 1.

ECG Measurements

Serum potassium, magnesium and calcium levels must be within normal limits before performing ECGs, as determined by local laboratory testing performed as specified in the main protocol TOC4129g/WO20698. Patients may receive electrolyte supplement per institutional standard practice to bring electrolyte levels within normal limits prior to performing the ECGs; retesting of potassium, magnesium, and calcium levels should be performed according to institutional standard practice.

Triplicate 12-lead ECG readings will be taken during the baseline period (Day −7 to Day −1; i.e., within 7 days prior to Cycle 1 Day 1) at the same time of day at which ECG measurements will be performed at Cycles 1 and 3.

To minimize postural variability, it is important that patients are resting and in a supine position for at least 10 minutes prior to each ECG collection. Blood draws and other procedures should be avoided during the period immediately before ECG measurement, and activity should be controlled as much as possible in order to minimize variability due to the effects of physiologic stress. Meals should be standardized as much as possible between patients, to avoid postprandial effects. If possible, ECGs should be collected on the same type of machine for each site involved in the study, and the same machine should be used for all ECGs for a specific patient. Detailed instructions on ECG acquisitions are provided in the central ECG core laboratory manual.

Triplicate runs of 12-lead ECG measurements must be obtained at each assessment timepoint, and should be collected over a period of 2 minutes (e.g., a single ECG each minute).

Assessments During Treatment

All visits and assessments during treatment are to be performed on the days indicated. Per the protocol described in Example 1, a cycle is 21 days in length.

ECG Measurements During Cycle 1 Day 1, Cycle 1 Day 3, and Cycle 3 Day 1

The 12-lead ECGs (triplicate runs) will be performed before collecting the corresponding PK samples. All ECGs for a patient should be obtained on the same machine.

Serum potassium, magnesium and calcium levels must be within normal limits before performing ECGs, as determined by local laboratory testing performed as specified in the main protocol TOC4129g/WO20698. Patients may receive electrolyte supplement per institutional standard practice to bring electrolyte levels within normal limits prior to performing the ECGs; retesting of potassium, magnesium, and calcium levels should be performed according to institutional standard practice.

Triplicate 12-lead ECG readings will be taken during Cycle 1 Day 1 and Cucle 3 Day 1 at the same time as the baseline ECG measurements, at the following times of day: 30 minutes and 15 minutes (±5 minutes) prior to pertuzumab/placebo infusion Any premedications that are required for pertuzumab/placebo infusions must be given between the two pre-infusion ECG measurements 0-15 minutes post-pertuzumab/placebo infusion
60-75 minutes post-pertuzumab/placebo infusion Triplicate 12-lead ECG readings will be also taken during Cycle 1 Day 3, post-docetaxel infusion and coincident with the 23-hour PK sample.

Pharmacokinetic Blood Samples

Unless otherwise specified, blood samples for PK evaluations should be drawn at the following timepoints:

Pre-dose: within 15 minutes before the infusion
Post-dose: within 15 minutes after the end of infusion Approximately 5 mL of blood will be drawn at each PK timepoint.

Pertuzumab Pharmacokinetics

Blood samples for pertuzumab PK evaluation will be drawn pre- and post-pertuzumab/placebo infusion at the following cycles: Cycles 1, 3, 6, 9, 12, 15, and 18. An additional sample will be drawn at the Treatment Discontinuation Visit (28-42 days after the last dose of study treatment).

At Cycles 1 and 3, the post-pertuzumab PK sample will be drawn 60-75 minutes after the end of the pertuzumab/placebo infusion (prior to administration of trastuzumab).

At Cycles 1 and 3, the pre-pertuzumab and 60-75 minutes post-pertuzumab PK samples must be collected after the corresponding ECGs are performed at those timepoints.

Trastuzumab Pharmacokinetics

Blood samples for trastuzumab PK evaluation will be drawn pre- and post-trastuzumab infusion at Cycles 1 and 3.

At Cycle 3, the trastuzumab dose should be delayed until after the 60-75 minute post-pertuzumab ECG assessments and PK sample collection have been completed.

Docetaxel Pharmacokinetics

Blood samples for docetaxel PK evaluation will be collected at Cycle 1 at the following timepoints after the initiation of the docetaxel infusion (Timepoint 0):

Cycle 1 Day 2
0.5 hour (during infusion)
1.0 hours (EOI)
1.25 hours (15 minutes after EOI)
2 hours (1 hour after EOI)
4 hours (3 hours after EOI)
6 hours (5 hours after EOI)
8 hours (7 hours after EOI)
Cycle 1: Day 3
24 hours (Cycle 1: Day 3, 23 hours after EOI)

Adverse Events

Adverse events will be collected and followed according to the requirements of the protocol of the study described in Example 1.

Assay Methods

Docetaxel Pharmacokinetic Assay

Plasma samples will be analyzed for docetaxel concentrations using a high-performance liquid chromatography (HPLC) method (or equivalent), and the plasma concentrations will be quantified by comparing the results against known standards. The lower limit of quantification (LLOQ)

for docetaxel in human plasma will be determined according to validated assay methods established by the laboratory contracted to perform the analyses.

Pertuzumab Pharmacokinetic Assay

Serum samples will be assayed for pertuzumab concentrations using an ELISA that is currently being developed. The minimum quantifiable concentration (MQC) for pertuzumab in human serum measured by this assay is to be determined.

Trastuzumab Pharmacokinetic Assay

Serum samples collected at baseline will be assayed for trastuzumab concentrations using a receptor-binding ELISA. This assay uses immobilized antigen HER2-ECD to capture trastuzumab from serum samples. The MQC for trastuzumab in human serum measured by this assay is 156 ng/mL.

Serum samples collected after pertuzumab administration will be assayed for trastuzumab concentrations using an ELISA that is currently being developed. The MQC for pertuzumab in human serum measured by this assay is to be determined.

Patient Discontinuation

Patients may voluntarily withdraw or be discontinued from this substudy at any time. Patients who withdraw from this substudy may continue participation in Study TOC4129g/WO20698. Reasons for patient discontinuation from the substudy include, but are not limited to, the following:

Voluntary withdrawal of consent

Non-compliance

Investigator determination that it is not in the patient's best interest to continue (e.g., illness or condition that requires the use of prohibited drugs or treatment)

Patient withdrawal from Protocol TOC4129g/WO20698

The primary reason for early discontinuation must be recorded on the appropriate electronic case report form (eCRF).

Statistical Methods

Due to the small sample size, the emphasis of all analyses will be on estimations. No formal statistical hypothesis testing is planned.

Analysis of the Conduct of the Study

Enrollment and discontinuations from this substudy will be summarized.

Analysis of Treatment Group Comparability

Demographic and baseline characteristics, such as age, sex, and race, will be summarized using means, standard deviations, medians, ranges (for continuous variables), and frequencies and percentages (for categorical variables). Summaries will be presented by study treatment patients actually received.

Pharmacokinetic Analyses

Population modeling will be used to derive post-hoc PK parameter estimates (CL, AUC, $V_d$, and $t_{1/2}$) for pertuzumab, and will be summarized for the treatment cohort. Observed $C_{max}$ and $C_{min}$ for pertuzumab and trastuzumab will be summarized for each specified PK sampling timepoint. Descriptive statistics will include means, medians, ranges, and standard deviations, as appropriate. Pertuzumab PK parameters and serum concentrationtime data will be compared with available data from other pertuzumab clinical studies.

PK samples for docetaxel will be obtained on Days 2 and 3 of Cycle 1 only. Plasma concentrations and the AUC for docetaxel will be summarized by treatment arm using descriptive statistics as described above. The geometric mean ratio for AUC between the experimental and control arms will be computed and the corresponding 90% confidence intervals will be provided.

Electrocardiogram Analyses

The ECG-evaluable analysis population will comprise all patients who receive any study drug (as per Protocol TOC4129g/WO20698) and who have ECG data available for baseline, the pre-pertuzumab/placebo timepoint on Cycle 1 Day 1, and at least one timepoint following pertuzumab/placebo administration at Cycle 1 or Cycle 3. The average of the triplicate ECG readings for each timepoint will be utilized in the analyses.

Descriptive statistics will be used for absolute QTcF value and change from baseline in QTcF for each timepoint. The difference in mean baseline-adjusted QTcF between the two treatment arms (ddQTcF) will be provided as well as the two-sided 90% confidence interval.

The time-matched, baseline-adjusted, and placebo-corrected QTcB, HR, PR, and QRS will be summarized in a similar fashion.

The number and percentage of patients with ECG recordings meeting the criteria as described in Section 3.2.2 will be tabulated for each treatment arm and each post-baseline time point as appropriate.

Missing Data

No missing ECG data will be imputed. As long as one of the triplicate ECGs is interpretable at each timepoint, a QTc will be calculated. If patients do not have corresponding ECGs at baseline and post-baseline timepoint of interest, they will not be included in the analysis for that timepoint.

Determination of Sample Size

At least 50 ECG-evaluable patients will be enrolled to this substudy. The sample size for this substudy has been primarily chosen to provide an estimate of key PK and ECG parameters. No formal statistical hypothesis testing is planned. Assuming an equal rate of participation between treatment arms (25 patients per treatment arm) and an estimated standard deviation of 20 ms, the two-sided 90% confidence interval for the baseline-adjusted difference in QTcF between treatment arms (ddQTcF) will be within 10 ms of the observed difference.

It is expected that at least 40 patients enrolled to this substudy will be PK-evaluable. A PK-evaluable patient is defined as a patient who has had complete PK samples collected at Cycle 1 and Cycle 3. With a sample size of 40 evaluable patients and an inter-patient coefficient of variation in AUC of 30%, the 90% confidence interval for the ratio of the geometric mean docetaxel concentrations between treatment arms will be (86%, 117%) if the observed geometric mean AUCs for both treatment arms are identical.

An ECG-evaluable patient is defined as a patient who has an interpretable baseline ECG as well as an interpretable ECG at Cycle 3 Day 1 immediately post-pertuzumab/placebo infusion (steady-state $C_{max}$). With this sample size of 40 evaluable patients and an estimated standard deviation of 20 ms, a 95% confidence interval for the difference between treatment arms in mean change in QTcF from baseline to Cycle 3 will be ±12.4 ms from the observed mean change.

What is claimed is:

1. A method for the treatment of a human patient with HER2 positive metastatic breast cancer who did not receive either prior chemotherapy or prior anti-HER2 therapy for their metastatic breast cancer, comprising administering to the patient an effective amount of a combination of pertuzumab, trastuzumab, and docetaxel, wherein treatment with the combination increases overall survival without increase in cardiac-specific adverse events relative to administration of trastuzumab and docetaxel in the absence of pertuzumab, wherein the pertuzumab is administered by intravenous infusion, at a fixed loading dose of 840 mg, followed by administration of a fixed dose of 420 mg every three weeks, the trastuzumab is administered by intravenous infusion at a loading dose of 8 mg/kg, followed by administration of a dose of 6 mg/kg every three weeks, and the docetaxel is administered by intravenous administration every three weeks for at least six cycles, wherein the initial dose of docetaxel is 75 mg/m$^2$ and is increased to 100 mg/m$^2$ if the patient tolerates the initial dose.

2. The method of claim 1, wherein the patient has a pre-treatment left ventricular ejection fraction (LVEF) ≥50%.

3. The method of claim 1, wherein the cardiac-specific adverse events are asymptomatic left ventricular ejection fraction (LVEF) event or congestive heart failure.

4. The method of claim 3, wherein the cardiac-specific adverse events are asymptomatic LVEF event and congestive heart failure.

5. A method for the treatment of a human patient with HER2 positive metastatic breast cancer who did not receive either prior chemotherapy or prior anti-HER2 therapy for their metastatic breast cancer and who has a pre-treatment left ventricular ejection fraction (LVEF) ≥50%, comprising administering to the patient an effective amount of a combination of pertuzumab, trastuzumab, and docetaxel, wherein treatment with the combination increases overall survival without increase in asymptomatic LVEF event and congestive heart failure relative to administration of trastuzumab and docetaxel in the absence of pertuzumab, wherein the pertuzumab is administered by intravenous infusion, at a fixed loading dose of 840 mg, followed by administration of a fixed dose of 420 mg every three weeks, the trastuzumab is administered by intravenous infusion at a loading dose of 8 mg/kg, followed by administration of a dose of 6 mg/kg every three weeks, and the docetaxel is administered by intravenous administration every three weeks for at least six cycles, wherein the initial dose of docetaxel is 75 mg/m$^2$ and is increased to 100 mg/m$^2$ if the patient tolerates the initial dose.

* * * * *

UNITED STATES PATENT AND TRADEMARK OFFICE
CERTIFICATE OF CORRECTION

PATENT NO. : 10,689,457 B2  
APPLICATION NO. : 15/293165  
DATED : June 23, 2020  
INVENTOR(S) : Virginia Paton et al.

Page 1 of 1

It is certified that error appears in the above-identified patent and that said Letters Patent is hereby corrected as shown below:

On the Title Page

In item (72), please add the following inventor:
--Graham Alexander Ross, Welwyn Garden City (GB)--.

In item (73), please add the following assignee:
--Hoffmann-La Roche Inc., Little Falls, NJ (US)--.

Signed and Sealed this
Twenty-fifth Day of March, 2025

Coke Morgan Stewart
*Acting Director of the United States Patent and Trademark Office*